United States Patent
Man et al.

(10) Patent No.: US 9,296,710 B2
(45) Date of Patent: *Mar. 29, 2016

(54) BICYCLO (3.1.0) HEXANE-2, 6-DICARBOXYLIC ACID DERIVATIVES AS MGLU2 RECEPTOR AGONIST

(75) Inventors: Teresa Tse Ki Man, Middlesex (GB); James Allen Monn, Indianapolis, IN (US); Carlos Montero Salgado, Madrid (ES); Lourdes Prieto, Madrid (ES); David Edward Tupper, Berkshire (GB); Lesley Walton, Berkshire (GB)

(73) Assignee: Eli Lilly and Company, Indianapolis, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/123,768

(22) PCT Filed: Jun. 7, 2012

(86) PCT No.: PCT/US2012/041229
§ 371 (c)(1),
(2), (4) Date: Dec. 4, 2013

(87) PCT Pub. No.: WO2012/173850
PCT Pub. Date: Dec. 20, 2012

(65) Prior Publication Data
US 2014/0113944 A1    Apr. 24, 2014

Related U.S. Application Data

(60) Provisional application No. 61/522,791, filed on Aug. 12, 2011.

(30) Foreign Application Priority Data

Jun. 17, 2011 (EP) .................................. 11382208

(51) Int. Cl.
*C07D 249/04* (2006.01)
*C07D 249/12* (2006.01)
*C07D 249/14* (2006.01)

(52) U.S. Cl.
CPC ............ *C07D 249/14* (2013.01); *C07D 249/04* (2013.01); *C07D 249/12* (2013.01)

(58) Field of Classification Search
CPC ... C07D 249/02; C07D 249/12; C07D 249/14
See application file for complete search history.

(56) References Cited

U.S. PATENT DOCUMENTS

| | | | |
|---|---|---|---|
| 5,688,826 A | 11/1997 | Massey et al. | |
| 5,849,525 A | 12/1998 | Hediger | |
| 5,958,960 A | 9/1999 | Massey et al. | |
| 6,316,498 B1 | 11/2001 | Nakazato et al. | |
| 6,333,428 B1 | 12/2001 | Nakazato et al. | |
| 6,716,452 B1 | 4/2004 | Piccariello et al. | |
| 6,770,676 B2 | 8/2004 | Nakazato et al. | |
| 7,038,077 B2 | 5/2006 | Dantzig et al. | |
| 7,067,507 B2 | 6/2006 | Pulley et al. | |
| 7,371,872 B2 | 5/2008 | Moher et al. | |
| 2005/0192273 A1 | 9/2005 | Johnson et al. | |
| 2011/0152334 A1* | 6/2011 | Monn et al. | 514/384 |

FOREIGN PATENT DOCUMENTS

| | | |
|---|---|---|
| EP | 0658539 A1 | 2/1994 |
| EP | 0774454 A1 | 5/1997 |
| EP | 1459765 A1 | 9/2004 |
| WO | 9306127 A1 | 4/1993 |
| WO | 9717952 A1 | 5/1997 |
| WO | 9718199 A1 | 5/1997 |
| WO | 9804277 A1 | 2/1998 |
| WO | 9851655 A1 | 11/1998 |
| WO | 9938839 A1 | 8/1999 |
| WO | 0012464 A1 | 3/2000 |
| WO | 0200605 A1 | 1/2002 |
| WO | 0234237 A1 | 5/2002 |
| WO | 02055481 A1 | 7/2002 |
| WO | 02055485 A1 | 7/2002 |
| WO | 03061698 A1 | 7/2003 |
| WO | 03084610 A1 | 10/2003 |
| WO | 03104217 A2 | 12/2003 |
| WO | 2011084437 A1 | 7/2011 |

OTHER PUBLICATIONS

Joseph P. Sanchez, John M. Domagala, Carl L. Heifetz, Stephen R. Priebe, Josephine A. Sesnie, and Ashok K. Trehan, "Quinolone Antibacterial Agents. Synthesis and Structure-Activity Relationships of a Series of Amino Acid Prodrugs of Racemic and Chiral 7-(3-Amino-1-pyrrolidinyl)quinolones. Highly Soluble Quinolone Prodrugs with in Vivo Pseudomonas Activity", Journal of Medicinal Chemistry, 1992, vol. 35, No. 10 1764-1773.

Koji Ohsumi, Toshihiro Hatanaka, Ryusuke Nakagawa, Yumiko Fukuda, Yoshihiro Morinaga, Yasuyo Suga, Yukio Nihei, Kazuo Ohishi, Yukio Akiyama and Takashi Tsuji, "Synthesis and antitumor activities of amino acid prodrugs of amino-combretastatins", Anti-Cancer Drug Design (1999), 14, 539-548.

Tracey D. Bradshaw, Michael C. Bibby, John A. Double, Iduna Fichtner, Patricia A. Cooper, Michael C. Alley, Susan Donohue, Sherman F. Stinson, Joseph E. Tomaszewjski, Edward A. Sausville, and Malcolm F. G. Stevens, "Preclinical Evaluation of Amino Acid Prodrugs of Novel Antitumor 2-(4-Amino-3-Methylphenyl)Benzothiazoles", Molecular Cancer Therapeutics (2002), 1, 239-246.

IUPAC-IUB Joint Commission on Biochemical Nomenclature (JCBN) Nomenclature and Symbolism for Amino Acids and Peptides, Eur J. Biochem, (1984) 138, 9-37.

Cheng Y. Yang, Anne H. Dantzig, and Charles Pidgeonk "Intestinal Peptide Transport Systems and Oral Drug Availability", Pharmaceutical Research, (1999), 16, 9, 1331-1343.

(Continued)

*Primary Examiner* — Sarah Pihonak
(74) *Attorney, Agent, or Firm* — R. Craig Tucker; Danica Hostettler

(57) ABSTRACT

The present invention provides novel mGlu2 agonists useful in the treatment of bipolar disorder, schizophrenia, and generalized anxiety disorder.

11 Claims, No Drawings

(56) References Cited

OTHER PUBLICATIONS

David Meredith, Catherine S. Temple, Nishan Guha, Corinna J. Sword, C. A. Richard Boyd, Ian D. Collier, Keith M. Morgan and Patrick D. Bailey, "Modified amino acids and peptides as substrates for the intestinal peptide transporter PepT1", Eur J. Biochem, (2000), 267, 3723-3728.

Kyoko Sawada, Tomohiro Terada, Hideyuki Saito, Yukiya Hashimoto, and Ken-Ichi Inui, "Recognition of L-Amino Acid Ester Compounds by Rat Peptide Transporters PEPT1 and PEPT2", The Journal of Pharmacology and Experimental Therapeutics (1999) 291, 705-709.

W. Clark Still, Michael Kahn, and Abhijit Mitra, "Rapid Chromatographic Technique for Preparative Separations with Moderate Resolution", (1978) J. Org Chem, 43, 14, 2923-2925.

P. K Smith, R. I. Krohn, G. T. Hermanson, A. K. Mallia, F. H. Gartner, M. D. Provenzano, E. K. Fujimoto, N. M. Goeke, B. J. Olson, and D. C. Klenk, "Measurement of Protein Using Bicinchoninic Acid" Analytical Biochemistry, (1985) 150, 76-85.

Hyo-kyung Han, Julie K. Rhie, Doo-Man Oh and Gordon L. Amidon, "Designing Prodrugs for the HPEPT1 Transporter", College of Pharmacy, The University of Michigan, pp. 259-260.

Anne H. Dantzig and Linda Bergin, "Uptake of the cephalosporin, cephalexin, by a dipeptide transport carrier in the human intestinal cell line, Caco-2", Biochimica et Biophysica Acda, (1990) 1027, 211-217.

James A. Monn, Steven M. Massey, Matthew J. Valli, Steven S. Henry, Gregory A. Stephenson, Mark Bures, Marc Herin, John Catlow, Deborah Giera, Rebecca A. Wright, Bryan G. Johnson, Sherri L. Andis, Arin Kingston, and Darryle D. Schoepp, "Synthesis and Metabotropic Glutamate Receptor Activity of S-Oxidized Variants of (-)4-Amino-2-thiabicyclo-13.1.0]hexane-4,6-dicarboxylate: Identification of Potent, Selective, and Orally Bioavailable Agonists for mGlu2/3 Receptors" J Med. Chem. (2007) 50, 233-240.

Hyo-Kyung Han, "Targeted Prodrug Design to Optimize Drug Delivery" AAPS Pharmsci (2000) 2(1) article 6, 1-11.

Ming Hu, Pullachipatti Subramanian, Henry I. Mosberg, and Gordon L. Amidon, "Use of the Peptide Carrier System to Improve the Intestinal Absorption of L-ox-Methyldopa: Carrier Kinetics, Intestinal Permeabilities, and in Vitro Hydrolysis of Dipeptidyl Derivatives of L-cx-Methyldopa", Pharmaceutical Research (1989) 6, 1, 66-70.

Hui-Po Wang, Jia-Shuai Lee, Ming-Cheng Tsai, Hsiao-Hwa Lu and Wenlie Hsu, "Synthesis and Pharmacological Activities of a Novel Tripeptide Mimetic Dopamine Prodrug" Bioorganic & Medicinal Chemistry Letters, (1995) 5, 19, 2195-2198.

Chun Yang, Giridhar S Tirucherai & Ashim K Mitra, "Prodrug based optimal drug delivery via membrane transporter/receptor" Exp. Opin. Biol. Ther; (2001) I(2):159-175.

"Amino acids, cyclic", http://www.nlm.nih.gov/cgi/mesh/2009/MB_cgi?mode=&term=Amino+Acids,+Cyclic&field=entry#TreeDI2.125.072, accessed Feb. 19, 2009.

"A Study for Patients with Schizophrenia", http://clinicaltrials.gov/ct2/show?terrn=schizophrenia+AND+LY+2140023&rank=2, accessed Sep. 20, 2010.

Volker Neugebauer & Susan M Carlton, "Peripheral metabotropic glutamate receptors as drug targets for pain relief", Expert Opinion on Therapeutic Targets (2002), 6(3), 349-361.

Georg Jaeschke, Joseph G Wettstein, Rebecca E Nordquist & Will Spooren, "mGlu5 receptor antagonists and their therapeutic potential", Expert Opinion on Therapeutic Patents, 2008, 18(2), pp. 123-142.

"Can schizophrenia be prevented", http://www.neuropsychiatryreviews.com/dec00/npr_dec00_schizo.html, accessed May 28, 2009.

Jayne Cartmell, James A. Monn & Darryle D. Schoepp, "Attenuation of specific PCP-evoked behaviors by the potent mGlu2V3 receptor agonist, LY379268 and comparison with the atypical antipsychotic, clozapine" Psychopharmacology (2000) 148:423-429.

Jayne Cartmell, James A. Monn, and Darryle D. Schoepp, "The Metabotropic Glutamate 2/3 Receptor Agonists LY354740 and LY379268 Selectively Attenuate Phencyclidine versus d-Amphetamine Motor Behaviors in Rats" JPET (1999) 291.161-170.

David R. Helton, Joseph P. Tizzano, James A. Monn, Darryle D. Schoepp and Mary Jeanne Kallman, "Anxiolytic and Side-Effect Profile of LY354740: A Potent, Highly Selective, Orally Active Agonist for Group 11 Metabotropic Glutamate Receptors" JPET (1998) 284, 651-660.

Esperanza R. Matarredona, Marti Santiago, Jose L. Venero, Josefina Cano and Alberto Machado, "Group II metabotropic glutamate receptor activation protects striatal dopaminergic nerve terminals against MPP+-induced neurotoxicity along with brain-derived neurotrophic factor induction", Journal of Neurochemistry, (2001) 76, 351-360.

J. Konieczny, K. Ossowska, S. Wolfarth, A. Pilc, "LY354740, a group 11 metabotropic glutamate receptor agonist with potential antiparkinsonian properties in rats", Naunyn-Schmiedeberg's Arch Pharmacol (1998) 358:500-502.

A. Shekhar, S.R. Keim, "LY354740, a potent group II metabotropic glutamate receptor agonist prevents lactate-induced panic-like response in panic-prone rats" Neuropharmacology 39 (2000) 1139-1146.

Aleksandra Klodzinska, Ewa Chojnacka-Wojcik, Agnieszka Palucha, Piotr Braniski, Piotr Popik, Andrzej Pilc, "Potential anti-anxiety, anti-addictive effects of LY 354740, a selective group II glutamate metabotropic receptors agonist in animal models", Neuropharmacology 38 (1999) 1831-1839.

Rosa Maria A. Simmons, Amy A. Webster, Anshu B. Kalra, Smriti Iyengar, "Group II mGluR receptor agonists are effective in persistent and neuropathic pain models in rats" Pharmacology, Biochemistry and Behavior 73 (2002) 419-427.

Jeong S Han, Yu Fu, Gary C Bird and Volker Neugebauer, "Enhanced group 11 mGluR-mediated inhibition of pain-related synaptic plasticity in the amygdala" Molecular Pain (2006), 2:18, 1-12.

V.J. Stella, W.N.A. Charman and v.H. Naringrekar, "Prodrugs: Do They Have Advantages in Clinical Practice?" Drugs (1985) 29: 455-473.

Jarkko Rautio, Hanna Kumpulainen, Tycho Heimbach, Reza Oliyai, Dooman Oh, Tomi Järvinen and Jouko Savolainen, "Prodrugs: design and clinical applications" Nature Reviews/Drug Discovery (2008) vol. 7, 255-270.

Jennifer M. Bossert, Shirley Y. Liu, Lin Lu, and Yavin Shaham, "Role of Ventral Tegmental Area Glutamate in Contextual Cue-Induced Relapse to Heroin Seeking" The Journal of Neurosience, Nov. 24, 2004, 24 (47):10726-10730.

Danielle S Counotte, et al., "Lasting synaptic changes underlie attention deficits caused by nicotine exposure during adolescence" Nature Neuroscience (2011) vol. 14, 417-419.

Jamie Peters, Peter W. Kalivas, "The group 11 metabotropic glutamate receptor agonist, LY379268, inhibits both cocaine- and food-seeking behavior in rats" Psychopharmacology (2006) 186: 143-149.

M. Foster Olive, Howard C Becker, Effects of the mGluR2/3 agonist LY379268 and the mGluR5 antagonist MPEP on handling-induced convulsions during ethanol withdrawal in mice (Alcohol, (2008), 42, 191-197.

Sandeep T Patil et al., "Activation of mGlu2/3 receptors as a new approach to treat schizophrenia: a randomized Phase 2 clinical trial" Nature Medicine (2007) vol. 13, 9, 1102-1107.

M.J. O'Neill, M.J. Fell, K.A. Svensson, J.M. Witkin and S.N. Mitchell, "Recent Developments in Metabotropic Glutamate Receptors as Novel Drug Targets" Drugs of the Future (2010) 35(4): 307-324.

* cited by examiner

BICYCLO (3.1.0) HEXANE-2, 6-DICARBOXYLIC ACID DERIVATIVES AS MGLU2 RECEPTOR AGONIST

This U.S. national stage application of International Application PCT/US2012/041229, filed Jun. 7, 2012, claims priority to European application 11382208, filed Jun. 17, 2011, and U.S. provisional application Ser. No. 61/522,791, filed Aug. 12, 2011.

The present invention relates to mGlu2 receptor agonist compounds, particular prodrugs thereof, and their salts as well as pharmaceutical compositions and therapeutic uses of such compounds, particular prodrugs, and their salts.

L-Glutamate is the major excitatory neurotransmitter in the central nervous system and is referred to as an excitatory amino acid. The metabotropic glutamate (mGlu) receptors are G-protein-coupled receptors that modulate neuronal excitability. Treatment of neurological or psychiatric disorders has been linked to selective activation of mGlu excitatory amino acid receptors. Various studies support Group II mGlu receptor (which includes mGlu2 and/or mGlu3) activation for the treatment of schizophrenia. More particularly, recent data demonstrate that an mGlu2/3 receptor agonist has antipsychotic properties and may provide a new alternative for the treatment of schizophrenia. Studies in mGlu2 and mGlu3 receptor knockout mice suggest that the antipsychotic-like activity of mGlu2/3 receptor agonists are mGlu2 mediated. Studies also demonstrate that mGlu2/3 agonists have anxiolytic, antidepressant, and neuroprotective properties. Therefore, mGlu2 receptor agonists may be useful in the treatment of psychiatric disorders, such as bipolar disorder (also known as manic depressive disorder), also known as manic depressive disorder, schizophrenia, and generalized anxiety disorder.

WO9717952 discloses certain 4-substituted bicyclo[3.1.0] hexane compounds asserted to be antagonists or agonists of metabotropic glutamate receptors. WO03104217 discloses bicyclo[3.1.0]hexane and heterobicyclo[3.1.0]hexane compounds asserted to be prodrug forms of mGlu2 receptor agonist compounds.

Excessive glutamatergic tone has been implicated in many disease states of the central nervous system; however, effective agents to correct such pathophysiological states are lacking in clinical practice. In particular, clinical application has not been realized due to a lack of mGlu2 agonists with appropriate drug-like properties. Thus, there still exists a need for potent mGlu2 agonists. There also exists a need for, efficacious mGlu2 agonists. The present invention provides novel 4-substituted bicyclo[3.1.0]hexanes, including particular prodrugs thereof which provide increased bioavailability suitable for clinical development, that are potent and effective mGlu2 agonists. Such new compounds of the present invention could address the need for potent, effective treatments of psychiatric disorders such as bipolar disorder, schizophrenia, and generalized anxiety disorder.

The present invention provides a compound of the formula:

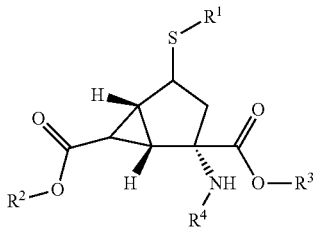

wherein $R^1$ is

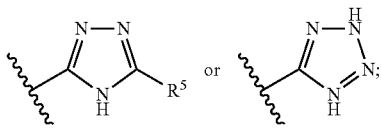

$R^2$ is hydrogen, 2,2-dimethyl-propionyloxymethyl, or benzyl, wherein benzyl is optionally substituted with one to two fluorine atoms, —$C_1$-$C_3$ alkyl optionally substituted with 1 to 3 fluorine atoms, or —$C_1$-$C_3$ alkoxy; $R^3$ is hydrogen, 2,2-dimethyl-propionyloxymethyl, or benzyl, wherein benzyl is optionally substituted with one to two fluorine atoms, —$C_1$-$C_3$ alkyl optionally substituted with 1 to 3 fluorine atoms, or —$C_1$-$C_3$ alkoxy; $R^4$ is hydrogen, (2S)-2-aminopropanoyl, (2S)-2-amino-4-methylsulfanyl-butanoyl, (2S)-2-amino-4-methyl-pentanoyl, or 2-aminoacetyl; $R^5$ is —$C_1$-$C_3$ alkyl optionally substituted with 1 to 3 fluorine atoms, —$NH_2$, or cyclopropyl; provided that when $R^2$ and/or $R^3$ are not hydrogen then $R^4$ is hydrogen; provided that when $R^4$ is not hydrogen then $R^2$ and/or $R^3$ are hydrogen; provided that $R^5$ may be hydrogen when the sulfur atom is attached to the bicyclo [3.1.0]hexane ring system in the S configuration; or a pharmaceutically acceptable salt thereof.

The present invention provides a method of treating a psychiatric disorder selected from the group consisting of bipolar disorder, schizophrenia, and generalized anxiety disorder comprising administering to a patient in need thereof an effective amount of a compound of the present invention or a pharmaceutically acceptable salt thereof.

The present invention also provides a method of treating pain comprising administering to a patient in need thereof an effective amount of a compound of the present invention or a pharmaceutically acceptable salt thereof.

The present invention also provides a method of treating substance abuse comprising administering to a patient in need thereof an effective amount of a compound of the present invention or a pharmaceutically acceptable salt thereof.

The present invention provides a pharmaceutical composition comprising a compound of the invention or a pharmaceutically acceptable salt thereof. The present invention provides a pharmaceutical composition comprising a compound of the invention or a pharmaceutically acceptable salt thereof, in combination with one or more pharmaceutically acceptable carriers, diluents, or excipients. In a particular embodiment, the formulation further comprises one or more other therapeutic agents.

The present invention provides a compound of the invention or a pharmaceutically acceptable salt thereof for use in therapy, in particular for the treatment of a psychiatric disorder. Further, the present invention provides the use of a compound of the invention or a pharmaceutically acceptable salt thereof for the manufacture of a medicament for the treatment of a psychiatric disorder. The present invention also provides a compound of the invention or a pharmaceutically acceptable salt thereof for use in the treatment of a psychiatric disorder.

The present invention provides a compound of the invention or a pharmaceutically acceptable salt thereof for use in therapy, in particular for the treatment of pain. Further, the present invention provides the use of a compound of the invention or a pharmaceutically acceptable salt thereof for the manufacture of a medicament for the treatment of pain. The present invention also provides a compound of the invention or a pharmaceutically acceptable salt thereof for use in the treatment of a pain.

The present invention provides a compound of the invention or a pharmaceutically acceptable salt thereof for use in therapy, in particular for the treatment of substance abuse. Further, the present invention provides the use of a compound of the invention or a pharmaceutically acceptable salt thereof for the manufacture of a medicament for the treatment of substance abuse. The present invention also provides a compound of the invention or a pharmaceutically acceptable salt thereof for use in the treatment of substance abuse.

Additionally, this invention provides a pharmaceutical formulation adapted for the treatment of a psychiatric disorder. Furthermore, the present invention provides preferred embodiments of the methods and uses as described herein, in which the psychiatric disorder is selected from the group consisting of bipolar disorder, schizophrenia, and generalized anxiety disorder.

Further, this invention provides a pharmaceutical formulation adapted for the treatment of pain. Even further, this invention provides a pharmaceutical formulation adapted for the treatment of substance abuse.

The general chemical terms used in the formulae above and throughout the specification have their usual meanings. For example, the term "—$C_1$-$C_3$ alkyl" is a —$C_1$-$C_3$ alkyl group and refers to methyl, ethyl, propyl, and iso-propyl. The term "—$C_1$-$C_3$ alkoxy" is a —$C_1$-$C_3$ alkyl group bonded to an oxygen atom and refers to methoxy, ethoxy, propoxy, and iso-propoxy.

The terms "nitrogen protecting group" or "amino protecting group" and "oxygen protecting group" or "carboxyl protecting group" are taken to mean a moiety that is stable to projected reaction conditions and yet may be selectively removed by reagents and reaction conditions compatible with the regenerated amine or acid. Such groups are well known by the skilled artisan and are described in the literature. See, e.g., Greene and Wuts, *Protective Groups in Organic Synthesis*, Fourth Edition, John Wiley & Sons, Inc., (2007).

The skilled artisan will appreciate that compounds of the invention can exist in tautomeric forms, as depicted for example in (1), below. When any reference in this application to one of the specific tautomers of the compounds of the invention is given, it is understood to encompass both tautomeric forms and all mixtures thereof

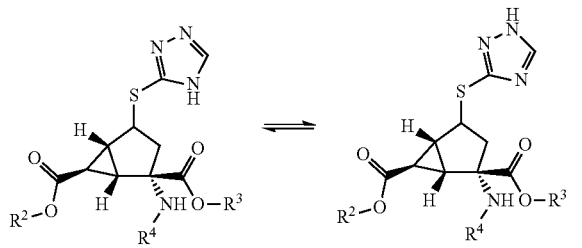

(1)

The skilled artisan will appreciate that compounds of the invention are comprised of a core that contains at least five chiral centers:

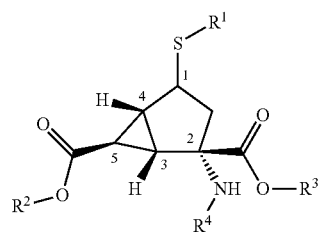

(2)

The compounds with the absolute configuration at the atoms labeled 2 through 5, as illustrated in (2) above, are preferred compounds of the invention. At the atom labeled 1, the R-configuration is defined when the sulfur atom is attached to the bicyclo[3.1.0]hexane ring system in the down position relative to planar position of the ring as indicated by a hashed bond. Conversely, the S-configuration is defined when the sulfur atom is attached to the bicyclo[3.1.0]hexane ring system in the up position relative to planar position of the ring as indicated by the solid wedge bond.

Additionally, the skilled artisan will appreciate that additional chiral centers may be created in the compounds of the invention by the selection of certain variables. In such an occurrence, the present invention contemplates all individual enantiomers or diastereomers, as well as mixtures of the enantiomers and diastereomers of said compounds including racemates.

The skilled artisan will also appreciate that the Cahn-Ingold-Prelog (R) or (S) designations for all chiral centers will vary depending upon the substitution patterns of the particular compound. The single enantiomers or diastereomers may be prepared beginning with chiral reagents or by stereoselective or stereospecific synthetic techniques. Alternatively, the single enantiomers or diastereomers may be isolated from mixtures by standard chiral chromatographic or crystallization techniques at any convenient point in the synthesis of compounds of the invention. Single enantiomers and diastereomers of compounds of the invention are a preferred embodiment of the invention.

The compounds of the present invention are capable of reaction, for example, with a number of inorganic and organic acids to form pharmaceutically acceptable acid addition salts or basic addition salts. Pharmaceutically acceptable salts and common methodology for preparing them are well known in the art. See, e.g., P. Stahl, et al. *Handbook of Pharmaceutical Salts: Properties, Selection and Use*, (VCHA/Wiley-VCH, 2002); S. M. Berge, et al., "Pharmaceutical Salts," *Journal of Pharmaceutical Sciences*, Vol. 66, No. 1, January 1977. Preferred pharmaceutically acceptable salts are those formed with hydrochloric acid.

Although all of the compounds of the invention are useful as agonists of mGlu2, certain classes of compounds are preferred. The following paragraphs describe such preferred classes:

$R^1$ is

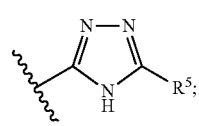

$R^1$ is

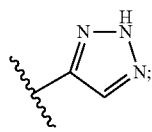

$R^2$ is hydrogen;

$R^2$ is 2,2-dimethyl-propionyloxymethyl, or benzyl optionally substituted with one to two fluorine atoms, —$CF_3$, or —$OCH_3$;

$R^2$ is hydrogen, 2,2-dimethyl-propionyloxymethyl, or benzyl optionally substituted with one to two fluorine atoms, —$CF_3$, or —$OCH_3$;

$R^2$ is benzyl optionally substituted with one to two fluorine atoms, —$CF_3$, or —$OCH_3$;

$R^3$ is hydrogen;

$R^3$ is 2,2-dimethyl-propionyloxymethyl, or benzyl optionally substituted with one to two fluorine atoms, —$CF_3$, or —$OCH_3$;

$R^3$ is benzyl optionally substituted with one to two fluorine atoms, —$CF_3$, or —$OCH_3$;

$R^3$ is hydrogen, 2,2-dimethyl-propionyloxymethyl, or benzyl optionally substituted with one to two fluorine atoms, —$CF_3$, or —$OCH_3$;

$R^4$ is hydrogen;

$R^4$ is (2S)-2-aminopropanoyl, (2S)-2-amino-4-methylsulfanyl-butanoyl, (2S)-2-amino-4-methyl-pentanoyl, or 2-aminoacetyl;

$R^5$ is $C_1$-$C_3$ alkyl optionally substituted with 1 to 3 fluorine atoms, —$NH_2$, or cyclopropyl;

The compound of the invention is a pharmaceutically acceptable salt;

The compound of the invention is the hydrochloride salt.

A preferred embodiment relates to compounds of the present invention wherein $R^1$ is

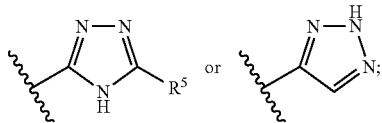

$R^2$ is hydrogen, 2,2-dimethyl-propionyloxymethyl, or benzyl, wherein benzyl is optionally substituted with one to two fluorine atoms, —$C_1$-$C_3$ alkyl optionally substituted with 1 to 3 fluorine atoms, or —$C_1$-$C_3$ alkoxy; $R^3$ is hydrogen, 2,2-dimethyl-propionyloxymethyl, or benzyl, wherein benzyl is optionally substituted with one to two fluorine atoms, —$C_1$-$C_3$ alkyl optionally substituted with 1 to 3 fluorine atoms, or —$C_1$-$C_3$ alkoxy; $R^4$ is hydrogen, (2S)-2-aminopropanoyl, (2S)-2-amino-4-methylsulfanyl-butanoyl, (2S)-2-amino-4-methyl-pentanoyl, or 2-aminoacetyl; $R^5$ is —$C_1$-$C_3$ alkyl optionally substituted with 1 to 3 fluorine atoms, —$NH_2$, or cyclopropyl; provided that when $R^2$ and/or $R^3$ are not hydrogen then $R^4$ is hydrogen; provided that when $R^4$ is not hydrogen then $R^2$ and/or $R^3$ are hydrogen; or a pharmaceutically acceptable salt thereof.

Another preferred embodiment relates to compounds of the present invention wherein $R^1$ is

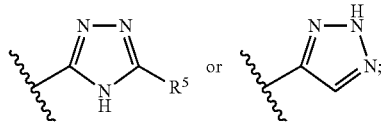

$R^2$ is hydrogen, 2,2-dimethyl-propionyloxymethyl, or benzyl optionally substituted with one to two fluorine atoms, —$CF_3$, or —$OCH_3$; $R^3$ is hydrogen, 2,2-dimethyl-propionyloxymethyl, or benzyl optionally substituted with one to two fluorine atoms, —$CF_3$, or —$OCH_3$; $R^4$ is hydrogen, (2S)-2-aminopropanoyl, (2S)-2-amino-4-methylsulfanyl-butanoyl, (2S)-2-amino-4-methyl-pentanoyl, or 2-aminoacetyl; $R^5$ is —$C_1$-$C_3$ alkyl optionally substituted with 1 to 3 fluorine atoms, —$NH_2$, or cyclopropyl; provided that when $R^2$ and/or $R^3$ are not hydrogen then $R^4$ is hydrogen; provided that when $R^4$ is not hydrogen then $R^2$ and/or $R^3$ are hydrogen; or a pharmaceutically acceptable salt thereof.

A further preferred embodiment relates to compounds of the present invention wherein $R^1$ is

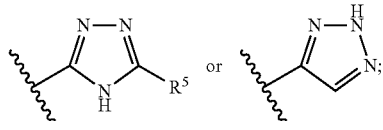

$R^2$ is hydrogen, 2,2-dimethyl-propionyloxymethyl, or benzyl optionally substituted with one to two fluorine atoms, —$CF_3$, or —$OCH_3$; $R^3$ is hydrogen, 2,2-dimethyl-propionyloxymethyl, or benzyl optionally substituted with one to two fluorine atoms, —$CF_3$, or —$OCH_3$; $R^4$ is hydrogen, (2S)-2-aminopropanoyl, (2S)-2-amino-4-methylsulfanyl-butanoyl, (2S)-2-amino-4-methyl-pentanoyl, or 2-aminoacetyl; $R^5$ is —$C_1$-$C_3$ alkyl optionally substituted with 1 to 3 fluorine atoms, —$NH_2$, or cyclopropyl; provided that when $R^2$ and/or $R^3$ are not hydrogen then $R^4$ is hydrogen; provided that when $R^4$ is not hydrogen then $R^2$ and/or $R^3$ are hydrogen; provided that $R^5$ may be hydrogen when the sulfur atom is attached to the bicyclo[3.1.0]hexane ring system in the S configuration; or a pharmaceutically acceptable salt thereof.

Another preferred embodiment relates to compounds of the present invention wherein $R^1$ is

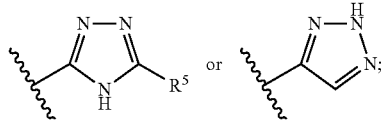

$R^2$ is hydrogen or benzyl optionally substituted with one to two fluorine atoms, —$CF_3$, or —$OCH_3$; $R^3$ is hydrogen or benzyl optionally substituted with one to two fluorine atoms, —$CF_3$, or —$OCH_3$; $R^4$ is hydrogen, (2S)-2-aminopropanoyl, (2S)-2-amino-4-methylsulfanyl-butanoyl, (2S)-2-amino-4-methyl-pentanoyl, or 2-aminoacetyl; $R^5$ is $C_1$-$C_3$ alkyl optionally substituted with 1 to 3 fluorine atoms, —$NH_2$, or cyclopropyl; provided that when $R^2$ and/or $R^3$ are not hydrogen then R⁴ is hydrogen; provided that when R⁴ is not hydrogen then R² and/or R³ are hydrogen; or a pharmaceutically acceptable salt thereof.

A further preferred embodiment relates to compounds of the present invention wherein R¹ is

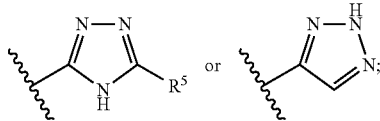

R² is hydrogen or benzyl optionally substituted with one to two fluorine atoms, —CF₃, or —OCH₃; R³ is hydrogen or benzyl optionally substituted with one to two fluorine atoms, —CF₃, or —OCH₃; R⁴ is hydrogen, (2S)-2-aminopropanoyl, (2S)-2-amino-4-methylsulfanyl-butanoyl, (2S)-2-amino-4-methyl-pentanoyl, or 2-aminoacetyl; R⁵ is C₁-C₃ alkyl optionally substituted with 1 to 3 fluorine atoms, —NH₂, or cyclopropyl; provided that when R² and/or R³ are not hydrogen then R⁴ is hydrogen; provided that when R⁴ is not hydrogen then R² and/or R³ are hydrogen; provided that R⁵ may be hydrogen when the sulfur atom is attached to the bicyclo[3.1.0]hexane ring system in the S configuration; or a pharmaceutically acceptable salt thereof.

A preferred embodiment relates to compounds of the present invention wherein R¹ is

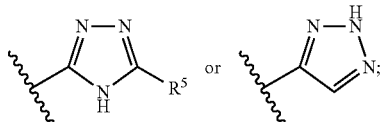

R² is 2,2-dimethyl-propionyloxymethyl, or benzyl optionally substituted with one to two fluorine atoms, —CF₃, or —OCH₃; R³ is 2,2-dimethyl-propionyloxymethyl, or benzyl optionally substituted with one to two fluorine atoms, —CF₃, or —OCH₃; R⁴ is hydrogen; R⁵ is C₁-C₃ alkyl optionally substituted with 1 to 3 fluorine atoms, —NH₂, or cyclopropyl; or a pharmaceutically acceptable salt thereof.

Another preferred embodiment relates to compounds of the present invention wherein R¹ is

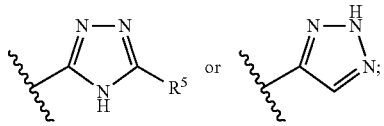

R² is 2,2-dimethyl-propionyloxymethyl, or benzyl optionally substituted with one to two fluorine atoms, —CF₃, or —OCH₃; R³ is 2,2-dimethyl-propionyloxymethyl, or benzyl optionally substituted with one to two fluorine atoms, —CF₃, or —OCH₃; R⁴ is hydrogen; R⁵ is C₁-C₃ alkyl optionally substituted with 1 to 3 fluorine atoms, —NH₂, or cyclopropyl; provided that R⁵ may be hydrogen when the sulfur atom is attached to the bicyclo[3.1.0]hexane ring system in the S configuration; or a pharmaceutically acceptable salt thereof.

An additional preferred embodiment relates to compounds of the present invention wherein R¹ is

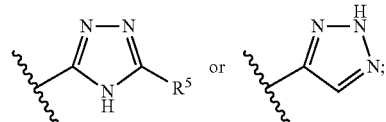

R² is benzyl optionally substituted with one to two fluorine atoms, —CF₃, or —OCH₃; R³ is benzyl optionally substituted with one to two fluorine atoms, —CF₃, or —OCH₃; R⁴ is hydrogen; R⁵ is C₁-C₃ alkyl optionally substituted with 1 to 3 fluorine atoms, —NH₂, or cyclopropyl; or a pharmaceutically acceptable salt thereof.

A further preferred embodiment relates to compounds of the present invention wherein R¹ is

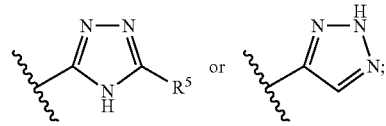

R² is benzyl optionally substituted with one to two fluorine atoms, —CF₃, or —OCH₃; R³ is benzyl optionally substituted with one to two fluorine atoms, —CF₃, or —OCH₃; R⁴ is hydrogen; R⁵ is C₁-C₃ alkyl optionally substituted with 1 to 3 fluorine atoms, —NH₂, or cyclopropyl; provided that R⁵ may be hydrogen when the sulfur atom is attached to the bicyclo[3.1.0]hexane ring system in the S configuration; or a pharmaceutically acceptable salt thereof.

Another further preferred embodiment relates to compounds of the present invention wherein R¹ is

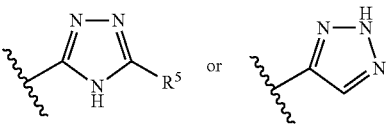

R² is hydrogen; R³ is hydrogen; R⁴ is (2S)-2-aminopropanoyl, (2S)-2-amino-4-methylsulfanyl-butanoyl, (2S)-2-amino-4-methyl-pentanoyl, or 2-aminoacetyl; R⁵ is C₁-C₃ alkyl optionally substituted with 1 to 3 fluorine atoms, —NH₂, or cyclopropyl; or a pharmaceutically acceptable salt thereof.

An additional further preferred embodiment relates to compounds of the present invention wherein R¹ is

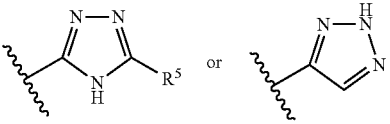

R² is hydrogen; R³ is hydrogen; R⁴ is (2S)-2-aminopropanoyl, (2S)-2-amino-4-methylsulfanyl-butanoyl, (2S)-2-amino-4-methyl-pentanoyl, or 2-aminoacetyl; R⁵ is C₁-C₃ alkyl optionally substituted with 1 to 3 fluorine atoms, —NH₂, or cyclopropyl; provided that R⁵ may be hydrogen when the sulfur atom is attached to the bicyclo[3.1.0]hexane ring system in the S configuration; or a pharmaceutically acceptable salt thereof.

An especially preferred embodiment relates to compounds of the present invention wherein R¹ is

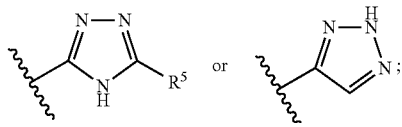

R² is hydrogen; R³ is hydrogen; R⁴ is hydrogen; R⁵ is C₁-C₃ alkyl optionally substituted with 1 to 3 fluorine atoms, —NH₂, or cyclopropyl; or a pharmaceutically acceptable salt thereof.

An especially preferred embodiment relates to compounds of the present invention wherein R¹ is

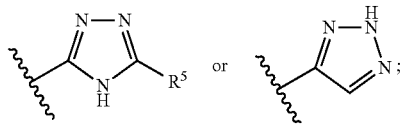

R² is hydrogen; R³ is hydrogen; R⁴ is hydrogen; R⁵ is C₁-C₃ alkyl optionally substituted with 1 to 3 fluorine atoms, —NH₂, or cyclopropyl; provided that R⁵ may be hydrogen when the sulfur atom is attached to the bicyclo[3.1.0]hexane ring system in the S configuration; or a pharmaceutically acceptable salt thereof.

Another especially preferred embodiment relates to compounds of the present invention wherein R¹ is

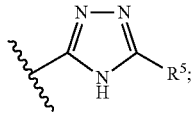

R² is hydrogen; R³ is hydrogen, R⁴ is hydrogen; R⁵ is C₁-C₃ alkyl optionally substituted with 1 to 3 fluorine atoms, —NH₂, or cyclopropyl; or a pharmaceutically acceptable salt thereof.

Another especially preferred embodiment relates to compounds of the present invention wherein R¹ is

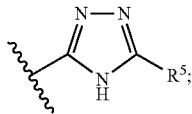

R² is hydrogen; R³ is hydrogen, R⁴ is hydrogen; R⁵ is C₁-C₃ alkyl optionally substituted with 1 to 3 fluorine atoms, —NH₂, or cyclopropyl; provided that R⁵ may be hydrogen when the sulfur atom is attached to the bicyclo[3.1.0]hexane ring system in the S configuration; or a pharmaceutically acceptable salt thereof.

The compounds of the present invention, or salts thereof, may be prepared by a variety of procedures known in the art, some of which are illustrated in the Schemes, Preparations, and Examples below. The specific synthetic steps for each of the routes described may be combined in different ways, or in conjunction with steps from different schemes, to prepare compounds of the invention, or salts thereof. The products of each step in the schemes below can be recovered by conventional methods, including extraction, evaporation, precipitation, chromatography, filtration, trituration, and crystallization.

Certain stereochemical centers have been left unspecified and certain substituents have been eliminated in the following schemes for the sake of clarity and are not intended to limit the teaching of the schemes in any way. Furthermore, individual isomers, enantiomers, or diastereomers may be separated at any convenient point in the synthesis of compounds of the invention by methods such as chiral chromatography. Additionally, the intermediates described in the following schemes contain a number of protecting groups for carboxyl and amino groups. The variable protecting group may be the same or different in each occurrence depending on the particular reaction conditions and the particular transformations to be performed. The protection and deprotection conditions are well known to the skilled artisan and are described in the literature. See. e.g., Greene and Wuts, *Protective Groups in Organic Synthesis*, supra.

The abbreviations used herein are defined according to *Aldrichimica Acta*, Vol. 17, No. 1, 1984. Other abbreviations are defined as follows: "tosylate" is p-toluenesulfonyl; "mesylate" is methanesulfonyl; "DIPEA" refers to diisopropylethylamine; "DIC" refers to diisopropylcarbodiimide; "HATU" refers to 2-(1H-7-azabenzotriazol-1-yl)-1,1,3,3-tetramethyl uronium hexafluorophosphate methanaminium "HBTU" refers to O-benzotriazole-N,N,N',N'-tetramethyluronium-hexafluoro-phosphate; "HOAt" refers to 1-hydroxy-7-azabenzotriazole; "PyBOP" refers to benzotriazol-1-yloxytripyrrolidino-phosphonium hexafluorophosphate; "PyBrop" refers to bromo-tris-pyrrolidino phosphonium-hexafluoro phosphate; "DMAP" refers to 4-dimethylaminopyridine; "THF" refers to tetrahydrofuran; "SCX" is strong cation exchange; "Prep No" is Preparation Number; "Ex No" is Example Number.

In the schemes below, all substituents unless otherwise indicated, are as previously defined. The reagents and starting materials are generally readily available to one of ordinary skill in the art. Others may be made by standard techniques of organic and heterocyclic chemistry which are analogous to the syntheses of known structurally-similar compounds and the procedures described in the Preparations and Examples which follow including any novel procedures.

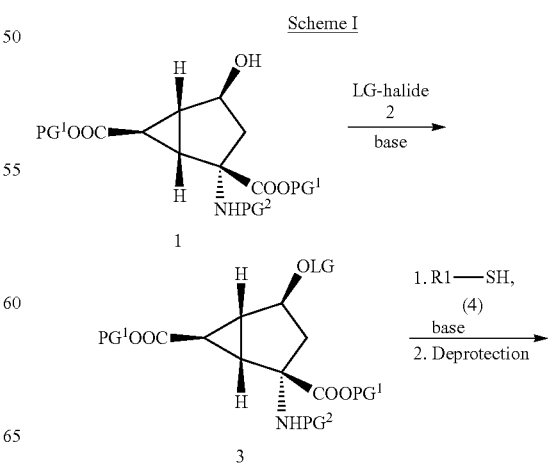

Scheme I

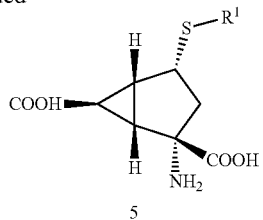

5

Scheme I illustrates the general synthesis of a compound of formula 5. "PG$^1$" is a protecting group developed for the carboxyl group, such as esters. "PG$^2$" is a protecting group developed for the amino group, such as carbamates and amides. Such protecting groups are well known and appreciated in the art. "LG" is a leaving group, such as tosylate or mesylate. Thus, "LG-halide" is a reagent, such as para-toluenesulfonyl chloride or methanesulfonyl chloride.

A compound of formula 1 reacts with a compound of formula 2 in the presence of an appropriate base, such as dimethylaminopyridine or triethylamine, in an appropriate solvent, such as dichloromethane, to provide a compound of formula 3. A compound of formula 5 results from the reaction of a compound of formula 3 with an appropriate compound of formula 4 in the presence of a suitable base, such as potassium carbonate or sodium carbonate, in an appropriate solvent, such as dimethylformamide, followed by conditions to facilitate the removal of the protecting groups, which are well known and appreciated in the art. A compound of formula 5 can be isolated as a free base or an appropriate salt, such as the hydrochloride salt.

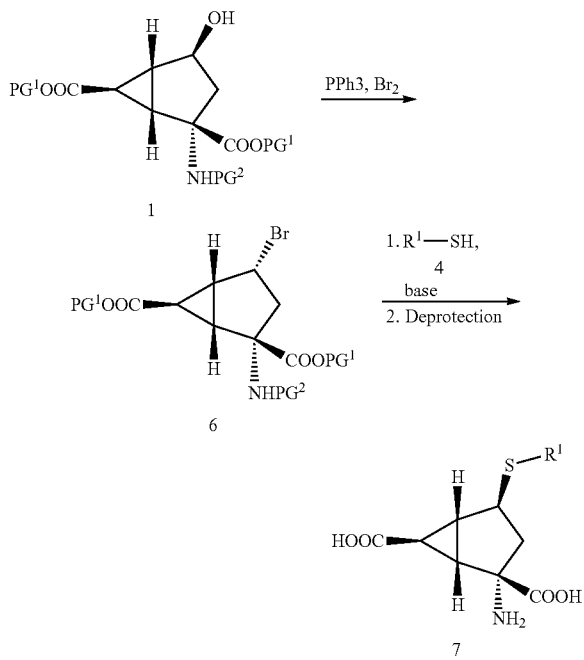

Scheme II illustrates the general synthesis of a compound of formula 7. "PG$^1$" and "PG$^2$" are the same as defined in Scheme I, above.

A compound of formula 1 is reacted with triphenyl phosphine and Br$_2$ in a suitable solvent, such as toluene or tetrahydrofuran, to provide the resulting bromo compound of formula 6. A compound of formula 7 results from the reaction of a compound of formula 6 with an appropriate compound of formula 4 in the presence of a suitable base, such as potassium carbonate, in an appropriate solvent, such as dimethylformamide, followed by conditions to facilitate the removal of the protecting groups, which are well known and appreciated in the art. A compound of formula 7 can be isolated as a free base or an appropriate salt, such as the hydrochloride salt.

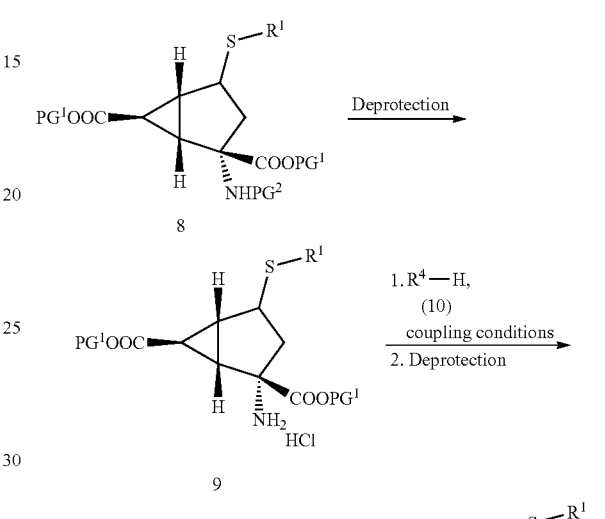

Scheme III illustrates the general synthesis to generate a compound of formula 11. "PG$^1$" and "PG$^2$" are the same as defined in Scheme I, above. R$^4$ is not hydrogen.

A compound of formula 8 is subjected to the appropriate deprotection conditions to effect removal of "PG$^2$" to yield a compound of formula 9. Such conditions are well known and appreciated in the art. A compound of formula 11 results from the reaction of a compound of formula 9 with a compound of formula 10 under appropriate coupling conditions followed by conditions to facilitate the removal of the protecting groups, which are well known and appreciated in the art. One skilled in the art will recognize that there are a number of methods and reagents for amide formation resulting from the reaction of carboxylic acids and amines. For example, appropriate coupling conditions include the reaction of an appropriate compound of formula 9 with an appropriate acid of formula 10 in the presence of a coupling reagent and an amine base, such as DIPEA or triethylamine Coupling reagents include carbodiimides, such as DCC, DIC, EDCI, and aromatic coupling reagents, such as HOBt and HOAt. Additionally, uronium or phosphonium salts of non-nucleophilic anions, such as HBTU, HATU, PyBOP, and PyBrOP can be used in place of the more traditional coupling reagents. Additives such as DMAP may be used to enhance the reactions. A compound of formula 11 can be isolated as a free base or an appropriate salt, such as the hydrochloride salt.

Scheme IV

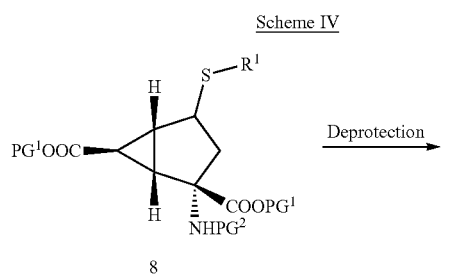

8

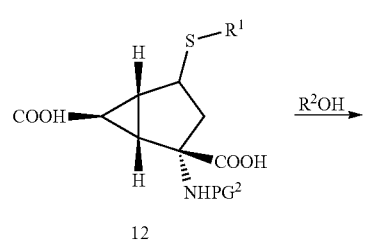

12

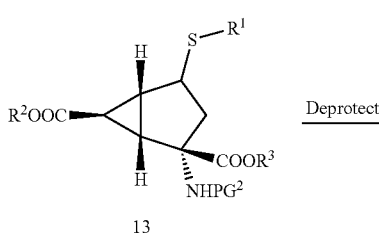

13

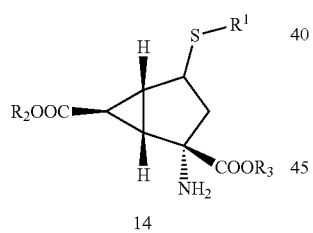

14

Scheme IV illustrates the general synthesis to generate a compound of formula 14. "PG$^1$" and PG$^2$" are defined as described in Scheme I above.

A compound of formula 12 is obtained by subjecting a compound of formula 8 to the appropriate deprotection conditions to effect the deprotection of the acids only. Such conditions are well known and appreciated in the art. A compound of formula 13 is obtained by esterification of the resulting free carboxylic acid moieties with R$^2$OH under the appropriate conditions. Note that R$^2$=R$^3$. The skilled artisan will appreciate that there are a number of methods and reagents to effect the esterification of a free carboxylic acid. For example, an excess of one of the reagents, such as the alcohol component, can be added to the reaction mixture. Alternatively, the resulting water can be removed from the reaction by distillation or dehydrating agent. Finally, the resulting compound of formula 13 is subjected to appropriate conditions to effect the deprotection of the amine Such conditions are well known and appreciated in the art. A compound of formula 14 can be isolated as a free base or an appropriate salt, such as the hydrochloride salt.

Alternatively, a di-ester wherein R$^2$ and R$^3$ are different can be achieved by selective and stepwise protection and deprotection of an appropriate intermediate, such as a compound of formula 7. Such conditions are well known and appreciated in the art.

As will be readily appreciated, compounds of formula 1 can be promptly prepared by methods similar to those described herein and by procedures that are well-known and established in the art. As will be readily understood, the steps to prepare the compounds of the present invention are dependent upon the particular compound being synthesized, the starting compound, and the relative lability of the substituted moieties.

PREPARATIONS AND EXAMPLES

The following preparations and examples further illustrate the invention.

The names for the exemplified compounds of the present invention are provided by SYMYX®Draw 3.2 or ACD/Name version 12.

Preparation 1

Ditert-butyl(1S,2S,4S,5R,6R)-2-(tert-butoxycarbonylamino)-4-(p-tolylsulfonyloxy)bicyclo[3.1.0]hexane-2,6-dicarboxylate

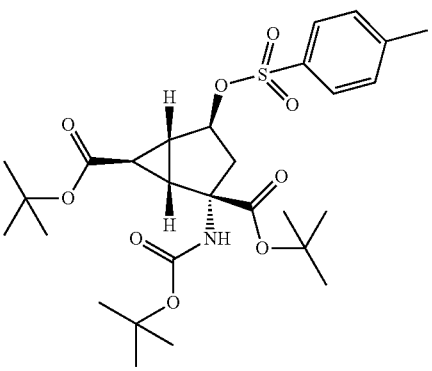 [SMILES: Cc1ccc(S(=O)(=O)O[C@H]2C[C@@](NC(=O)OC(C)(C)C)(C(=O)OC(C)(C)C)[C@@H]3[C@@H](C(=O)OC(C)(C)C)[C@@H]32)cc1]

Charge a 2-necked round bottom flask under nitrogen atmosphere with ditert-butyl(1S,2S,4S,5R,6R)-2-(tert-butoxycarbonylamino)-4-hydroxy-bicyclo[3.1.0]hexane-2,6-dicarboxylate (20.7 g, 0.5 mol, see WO03/104217/A2 for synthesis details), 4-dimethylaminopyridine (10.4 g, 0.85 mol), triethylamine (6.98 mL, 0.5 mmol) and p-toluenesulfonyl chloride (10.6 g, 0.55 mol) in dichloromethane (200 mL), and stir the mixture at room temperature overnight. Add 1N solution of potassium hydrogen sulfate (200 mL), water (100 mL) and extract the organic layer. Wash with water (200 mL), brine (200 mL), dry over magnesium sulfate, filter and evaporate to dryness. Add tetrahydrofuran (30 mL) then heptanes (90 mL). Heat the mixture at 60° C. and slowly add more heptanes (200 mL). Cool the mixture to room temperature. Filter the solid and dry under reduced pressure to yield the title compound as a white solid (24.6 g, 87%). MS (m/z): 590 (M+23).

Preparation 2

Ditert-butyl(1R,2S,4R,5R,6R)-4-bromo-2-(tert-butoxycarbonylamino)bicyclo[3.1.0]hexane-2,6-dicarboxylate

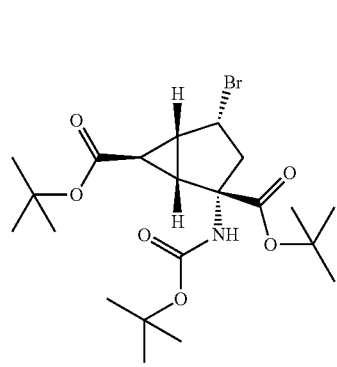 [SMILES: CC(C)(C)OC(=O)N[C@@]1(C(=O)OC(C)(C)C)C[C@@H](Br)[C@H]2[C@H](C(=O)OC(C)(C)C)[C@H]21]

Dissolve triphenylphosphine (41.97 g, 158.4 mmol) in fresh toluene (660 mL) and add bromine (8.14 mL, 158.4 mmol) until a yellow color persists. Add dropwise a solution of ditert-butyl(1S,2S,4S,5R,6R)-2-(tert-butoxycarbonylamino)-4-hydroxy-bicyclo[3.1.0]hexane-2,6-dicarboxylate (32.75 g, 79.2 mmol) in toluene (176 mL) and anhydrous pyridine (528 mL) during 45 min. Stir the reaction at 75° C. overnight. Cool to room temperature, dilute with ethyl acetate, filter and concentrate to dryness. Slurry the crude in methyl tert-butyl ether, filter to remove the solids and concentrate the filtrate to dryness. Purify the crude by silica gel chromatography (750 g) eluting with hexane:ethyl acetate (0:100 to 80:20) to obtain the title compound as a white solid (29.52 g, 78%). MS (m/z): 498, 500 (M+23).

Preparation 3

Ditert-butyl(1R,2S,4S,5R,6R)-2-(tert-butoxycarbonylamino)-4-(1H-1,2,4-triazol-3-ylsulfanyl)bicyclo[3.1.0]hexane-2,6-dicarboxylate

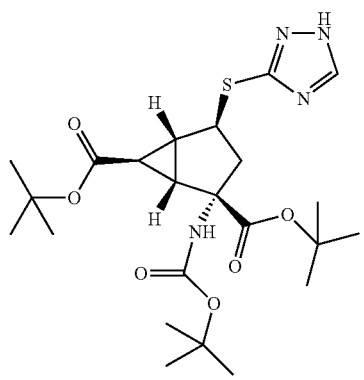 [SMILES: CC(C)(C)OC(=O)N[C@@]1(C(=O)OC(C)(C)C)C[C@H](Sc2nc[nH]n2)[C@H]2[C@H](C(=O)OC(C)(C)C)[C@H]21]

Add to a solution of ditert-butyl(1R,2S,4R,5R,6R)-4-bromo-2-(tert-butoxycarbonylamino)bicyclo[3.1.0]hexane-2,6-dicarboxylate (2 g, 4.20 mmol) in dimethylformamide (10 mL), 1H-1,2,4-triazole-3-thiol (525 mg, 5.04 mmol) and potassium carbonate (1.16 g, 8.4 mmol). Stir the mixture at 80° C. overnight. Cool to room temperature and dilute with ethyl acetate, wash with 10% citric acid and brine, dry over anhydrous sodium sulfate, filter and concentrate to dryness. Purify by silica gel chromatography (80 g silica column) eluting with hexane:ethyl acetate (80:20 to 0:100) to obtain the title compound (1.64 g, 78%). MS (m/z): 497 (M+1).

The following compounds in Table 1 are prepared from Preparation 1 or Preparation 2 by essentially following the method of preparation 3.

TABLE 1

| Prep No. | Chemical Name | Structure | Physical Data M (m/z): |
|---|---|---|---|
| 4 | Ditert-butyl (1R,2S,4R,5R,6R)-2-(tert-butoxycarbonylamino)-4-[[5-(difluoromethyl)-4H-1,2,4-triazol-3-yl]sulfanyl]bicyclo[3.1.0]hexane-2,6-dicarboxylate | 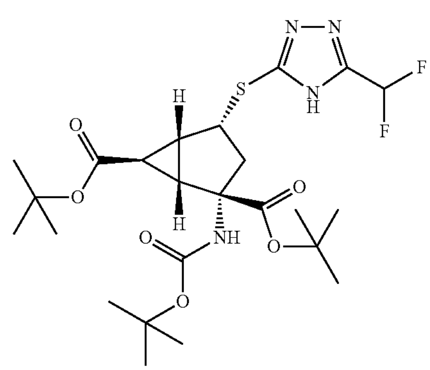 [SMILES: CC(C)(C)OC(=O)N[C@@]1(C(=O)OC(C)(C)C)C[C@@H](Sc2nnc(C(F)F)[nH]2)[C@H]2[C@H](C(=O)OC(C)(C)C)[C@H]21] | 569 (M + 23) |

TABLE 1-continued

| Prep No. | Chemical Name | Structure | Physical Data M (m/z): |
|---|---|---|---|
| 5 | Ditert-butyl(1R,2S,4R,5R,6R)-4-(5-amino-[1,3,4]triazol-2-ylsulfanyl)-2-tert-butoxycarbonylamino-bicyclo[3.1.0]hexane-2,6-dicarboxylate[1] | 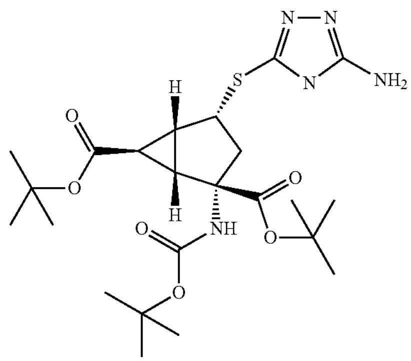 [SMILES: CC(C)(C)OC(=O)N[C@@]1(C(=O)OC(C)(C)C)C[C@@H](Sc2nnc(N)[nH]2)[C@H]2[C@H](C(=O)OC(C)(C)C)[C@H]21] | 512 (M + 1). |
| 6 | Ditert-butyl (1R,2S,4R,5R,6R)-2-(tert-butoxycarbonylamino)-4-[(5-methyl-4H-1,2,4-triazol-3-yl)sulfanyl]bicyclo[3.1.0]hexane-2,6-dicarboxylate | 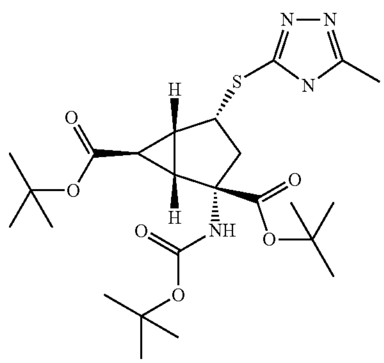 [SMILES: Cc1nnc(S[C@@H]2C[C@@](NC(=O)OC(C)(C)C)(C(=O)OC(C)(C)C)[C@@H]3[C@@H](C(=O)OC(C)(C)C)[C@@H]32)[nH]1] | 511 (M + 1) |
| 7 | Ditert-butyl (1R,2S,4R,5R,6R)-2-(tert-butoxycarbonylamino)-4-[(5-isopropyl-4H-1,2,4-triazol-3-yl)sulfanyl]bicyclo[3.1.0]hexane-2,6-dicarboxylate | 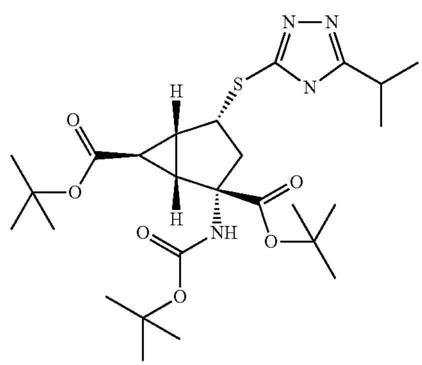 [SMILES: CC(C)c1nnc(S[C@@H]2C[C@@](NC(=O)OC(C)(C)C)(C(=O)OC(C)(C)C)[C@@H]3[C@@H](C(=O)OC(C)(C)C)[C@@H]32)[nH]1] | 539 (M + 1) |
| 8 | Ditert-butyl (1R,2S,4R,5R,6R)-2-(tert-butoxycarbonylamino)-4-[(5-cyclopropyl-4H-1,2,4-triazol-3-yl)sulfanyl]bicyclo[3.1.0]hexane-2,6-dicarboxylate | 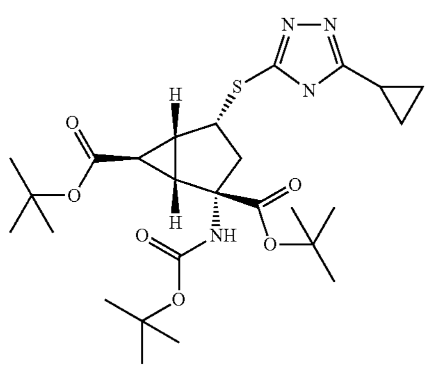 [SMILES: CC(C)(C)OC(=O)N[C@@]1(C(=O)OC(C)(C)C)C[C@@H](Sc2nnc(C3CC3)[nH]2)[C@H]2[C@H](C(=O)OC(C)(C)C)[C@H]21] | 537 (M + 1) |

TABLE 1-continued

| Prep No. | Chemical Name | Structure | Physical Data M (m/z): |
|---|---|---|---|
| 9 | Ditert-butyl (1R,2S,4S,5R,6R)-2-(tert-butoxycarbonylamino)-4-[(5-cyclopropyl-4H-1,2,4-triazol-3-yl)sulfanyl]bicyclo[3.1.0]hexane-2,6-dicarboxylate | 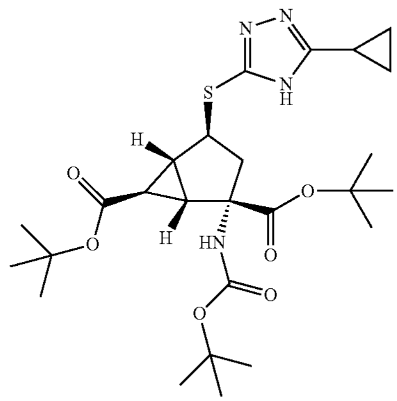 [SMILES: CC(C)(C)OC(=O)N[C@@]1(C(=O)OC(C)(C)C)C[C@H](Sc2nnc(C3CC3)[nH]2)[C@H]2[C@H](C(=O)OC(C)(C)C)[C@H]21] | 537 (M + 1). |
| 10 | Ditert-butyl (1R,2S,4S,5R,6R)-2-(tert-butoxycarbonylamino)-4-[(5-isopropyl-4H-1,2,4-triazol-3-yl)sulfanyl]bicyclo[3.1.0]hexane-2,6-dicarboxylate[2] | 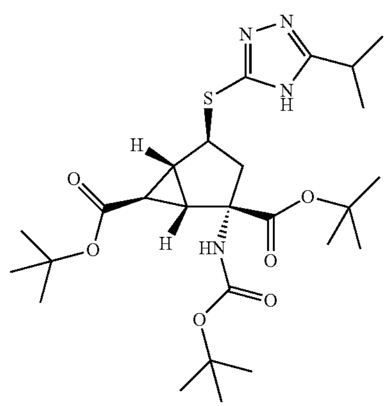 [SMILES: CC(C)c1nnc(S[C@H]2C[C@@](NC(=O)OC(C)(C)C)(C(=O)OC(C)(C)C)[C@@H]3[C@@H](C(=O)OC(C)(C)C)[C@@H]32)[nH]1] | 539 (M + 1) |
| 11 | Ditert-butyl (1R,2S,4S,5R,6R)-2-(tert-butoxycarbonylamino)-4-[(5-methyl-4H-1,2,4-triazol-3-yl)sulfanyl]bicyclo[3.1.0]hexane-2,6-dicarboxylate[2] | 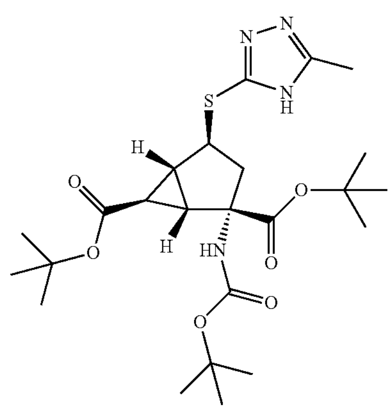 [SMILES: Cc1nnc(S[C@H]2C[C@@](NC(=O)OC(C)(C)C)(C(=O)OC(C)(C)C)[C@@H]3[C@@H](C(=O)OC(C)(C)C)[C@@H]32)[nH]1] | 511 (M + 1) |

TABLE 1-continued

| Prep No. | Chemical Name | Structure | Physical Data M (m/z): |
|---|---|---|---|
| 12 | Ditert-butyl (1R,2S,4S,5R,6R)-4-[(5-amino-1H-1,2,4-triazol-3-yl)sulfanyl]-2-(tert-butoxycarbonylamino)bicyclo[3.1.0]hexane-2,6-dicarboxylate[2] | 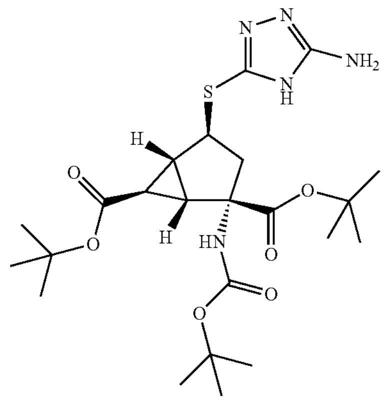 [SMILES: CC(C)(C)OC(=O)N[C@@]1(C(=O)OC(C)(C)C)C[C@H](Sc2nnc(N)[nH]2)[C@H]2[C@H](C(=O)OC(C)(C)C)[C@H]21] | 512 (M + 1). |

[1]The base used in the reaction is $Na_2CO_3$.
[2]Heat the reaction via microwave.

Preparation 13

Ditert-butyl(1R,2S,4R,5R,6R)-2-(tert-butoxycarbonylamino)-4-[[5-(trifluoromethyl)-1H-1,2,4-triazol-3-yl]sulfanyl]bicyclo[3.1.0]hexane-2,6-dicarboxylate

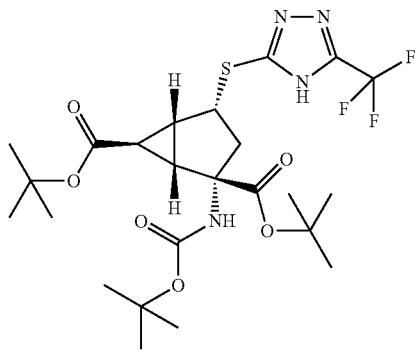 [SMILES: CC(C)(C)OC(=O)N[C@@]1(C(=O)OC(C)(C)C)C[C@@H](Sc2nnc(C(F)(F)F)[nH]2)[C@H]2[C@H](C(=O)OC(C)(C)C)[C@H]21]

Purge with nitrogen a solution of ditert-butyl(1R,2S,4R,5R,6R)-2-(tert-butoxycarbonylamino)-4-(2H-triazol-4-yl-sulfanyl)bicyclo[3.1.0]hexane-2,6-dicarboxylate (11.8 mg, 20.77 mmol) and 1H-mercapto-(trifluoromethyl)-4H-1,2,4-triazole, sodium salt (7.7 g, 38.5 mmol) in dimethylformamide (100 mL) and stir at 70° C. overnight. Cool to room temperature, dilute with water and extract with ethyl acetate. Wash the organic layer with water, brine, dry over magnesium sulfate and concentrate to dryness. Purify by flash column chromatography eluting with isohexane:ethyl acetate (95:5 to 60:40) to yield the title compound (10.9 g, 93.5%). MS (m/z): 587 (M+23).

The following compounds in Table 2 are prepared essentially following method of preparation 13.

TABLE 2

| Prep No. | Chemical Name | Structure | Physical Data M (m/z) |
|---|---|---|---|
| 14 | Ditert-butyl (1R,2S,4R,5R,6R)-2-(tert-butoxycarbonylamino)-4-(2H-1,2,4-triazol-4-ylsulfanyl)bicyclo[3.1.0]hexane-2,6-dicarboxylate | 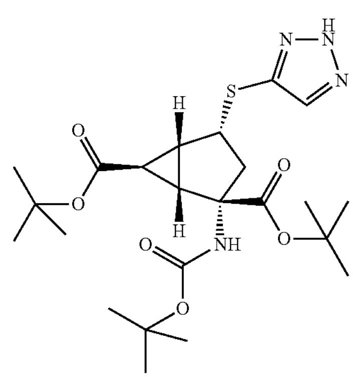 | 519 (M + 23) |

TABLE 2-continued

| Prep No. | Chemical Name | Structure | Physical Data M (m/z) |
|---|---|---|---|
| 15 | Ditert-butyl (1R,2S,4S,5R,6R)-2-(tert-butoxycarbonylamino)-4-(1H-1,2,3-triazol-5-ylsulfanyl)bicyclo[3.1.0]hexane-2,6-dicarboxylate[2] | 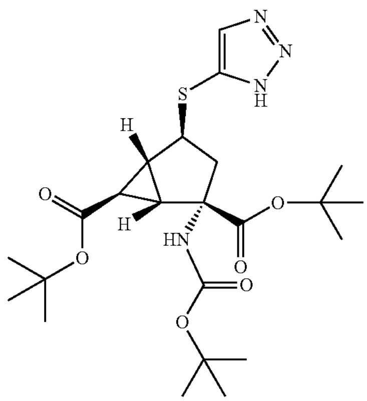 [SMILES: CC(C)(C)OC(=O)N[C@@]1(C(=O)OC(C)(C)C)C[C@H](Sc2cnn[nH]2)[C@H]2[C@H](C(=O)OC(C)(C)C)[C@H]21] | 497 (M + 1) |
| 16 | Ditert-butyl (1R,2S,4S,5R,6R)-2-(tert-butoxycarbonylamino)-4-[[5-(trifluoromethyl)-1H-1,2,4-triazol-3-yl]sulfanyl]bicyclo[3.1.0]hexane-2,6-dicarboxylate[2] | 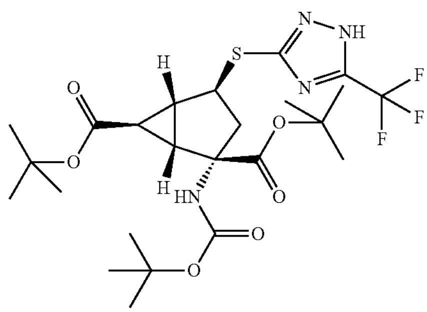 [SMILES: CC(C)(C)OC(=O)N[C@@]1(C(=O)OC(C)(C)C)C[C@H](Sc2n[nH]c(C(F)(F)F)n2)[C@H]2[C@H](C(=O)OC(C)(C)C)[C@H]21] | 587 (M + 23) |
| 17 | Ditert-butyl (1R,2S,4S,5R,6R)-2-(tert-butoxycarbonylamino)-4-[[5-(difluoromethyl)-4H-1,2,4-triazol-3-yl]sulfanyl]bicyclo[3.1.0]hexane-2,6-dicarboxylate | 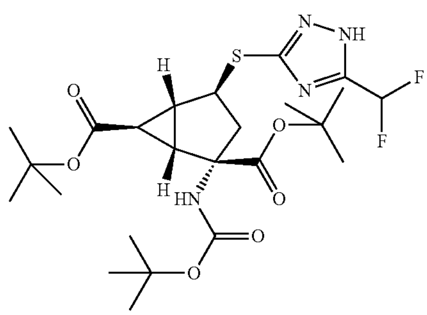 [SMILES: CC(C)(C)OC(=O)N[C@@]1(C(=O)OC(C)(C)C)C[C@H](Sc2n[nH]c(C(F)F)n2)[C@H]2[C@H](C(=O)OC(C)(C)C)[C@H]21] | 569 (M + 23) |

[2]Heat the reaction via microwave.

Preparation 18

Diethyl(1R,2S,4S,5R,6R)-2-amino-4-(1H-[1,2,4]triazol-3-ylsulfanyl)-bicyclo[3.1.0]hexane-2,6-dicarboxylate hydrochloride

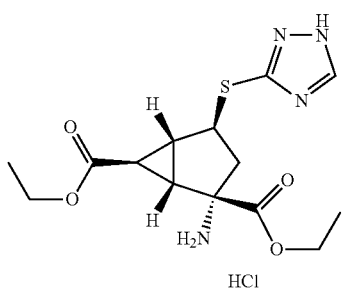 [SMILES: CCOC(=O)[C@H]1[C@H]2[C@@H]1[C@](N)(C(=O)OCC)C[C@@H]2Sc1nc[nH]n1 ; Cl]

Charge a round bottom flask with ditert-butyl(1R,2S,4S,5R,6R)-2-(tert-butoxycarbonylamino)-4-(4H-1,2,4-triazol-3-ylsulfanyl)bicyclo[3.1.0]hexane-2,6-dicarboxylate (3.7 g, 7.45 mmol) and ethanol (50 mL). Add slowly thionyl chloride (2.71 mL, 37.25 mmol) (exothermic reaction to 45° C.) and stir the mixture at 80° C. overnight. Remove the solvent under vacuum to give the title compound as a white solid (2.8 g, 99%). MS (m/z): 341 (M+1).

The following compounds in Table 3 are prepared essentially following the method of preparation 18.

TABLE 3

| Prep No. | Chemical Name | Structure | Physical data (MS (m/z)) |
|---|---|---|---|
| 19 | Diethyl (1R,2S,4R,5R,6R)-2-Amino-4-(2H-[1,2,3]triazol-4-ylsulfanyl)-bicyclo[3.1.0]hexane-2,6-dicarboxylate hydrochloride | 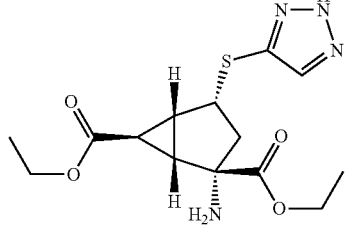 | 341 (M + 1), 363 (M + 23) |
| 20 | Diethyl (1R,2S,4R,5R,6R)-2-Amino-4-(5-trifluoromethyl-1H-[1,2,4]triazol-3-ylsulfanyl)-bicyclo[3.1.0]hexane-2,6-dicarboxylate hydrochloride | 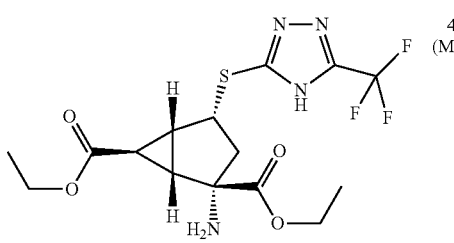 | 409 (M + 1) |

Preparation 21

Diethyl(1R,2S,4S,5R,6R)-2-[[-2-(tert-butoxycarbonylamino)acetyl]amino]-4-(4H-1,2,4-triazol-3-ylsulfanyl)bicyclo[3.1.0]hexane-2,6-dicarboxylate

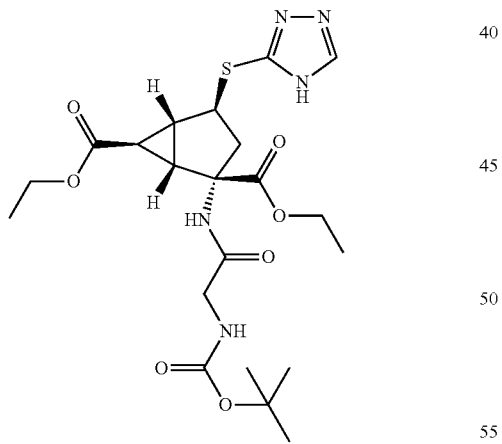

To diethyl(1R,2S,4S,5R,6R)-2-amino-4-(4H-1,2,4-triazol-3-ylsulfanyl)bicyclo[3.1.0]hexane-2,6-dicarboxylate hydrochloride (0.869 g, 2.31 mmol) add tetrahydrofuran (11.5 mL) and cool the mixture to 0-5° C. with an ice water bath. Add 2-chloro-4,6-dimethoxy-1,3,5-triazine (404.9 mg, 2.31 mmol) and (2S)-2-(tert-butoxycarbonylamino)acetic acid (0.404 g, 2.31 mmol). Slowly add N-methylmorpholine (0.55 mL, 5.07 mmol) and stir for 2 hours. Filter the mixture and wash the white solid with tetrahydrofuran. Discard the solid and concentrate the solution to dryness. Purify by OASIS® HLB cartridge (load in DMSO and elute with ammonium bicarbonate buffer solution pH=9/acetonitrile gradient). Desired compound elute with 3:1 (ammonium bicarbonate/acetonitrile). Remove the solvent. Dissolve the residue in dichloromethane and wash with water. Discard the aqueous phase. Dry over magnesium sulfate, filter and concentrate to dryness to yield the title compound as a white solid (440 mg, 38%). MS (m/z): 498 (M+1), 520 (M+23).

Preparation 22

Diethyl(1R,2S,4S,5R,6R)-2-((S)-2-tert-butoxycarbonylamino-propionylamino)-4-(4H-[1,2,4]triazol-3-ylsulfanyl)-bicyclo[3.1.0]hexane-2,6-dicarboxylate

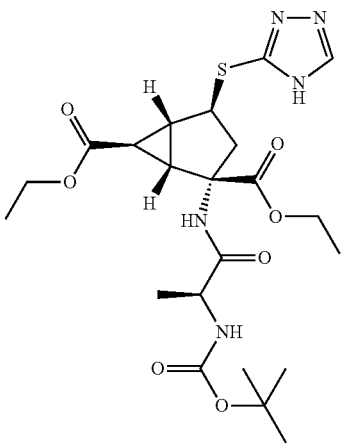 [SMILES: CCOC(=O)[C@H]1[C@H]2[C@@H]1[C@](NC(=O)[C@H](C)NC(=O)OC(C)(C)C)(C(=O)OCC)C[C@@H]2Sc1nnc[nH]1]

Combine diethyl(1R,2S,4S,5R,6R)-2-amino-4-(4H-1,2,4-triazol-3-ylsulfanyl)bicyclo[3.1.0]hexane-2,6-dicarboxylate hydrochloride (354 mg, 0.894 mmol), (2S)-2-(tert-butoxycarbonylamino)propanoic acid (257 mg, 1.34 mmol), 4-dimethylaminopyridine (10.92 mg, 89 μmol), 1-hydroxybenzotriazole hydrate (219 mg, 1.41 mmol) and 1-(3-dimethylaminopropyl)-3-ethylcarbodiimide hydrochloride (208 mg, 1.34 mmol) in dichloromethane (9 mL) and add triethylamine (373 μL, 2.68 mmol). Stir the mixture at room temperature overnight under a nitrogen atmosphere. Wash with 10% citric acid solution, saturated sodium hydrogencarbonate solution and brine. Discard the aqueous layers, filter the organic layer through a diatomaceous earth cartridge and remove the solvent under vacuum. Purify by flash chromatography eluting with dichloromethane:methanol (1-15%) to yield the title compound (412.5 mg, 90.2%). MS (m/z): 552 (M+1), 534 (M+23).

The following compounds in Table 4 are prepared essentially following method of Preparation 22.

TABLE 4

| Prep. No. | Chemical Name | Structure | Physical data MS (m/z) |
|---|---|---|---|
| 23 | Diethyl (1R,2S,4S,5R,6R)-2-((S)-2-tert-butoxycarbonylamino-4-methyl-pentanoylamino)-4-(4H-[1,2,4]triazol-3-ylsulfanyl)-bicyclo[3.1.0]hexane-2,6-dicarboxylate | 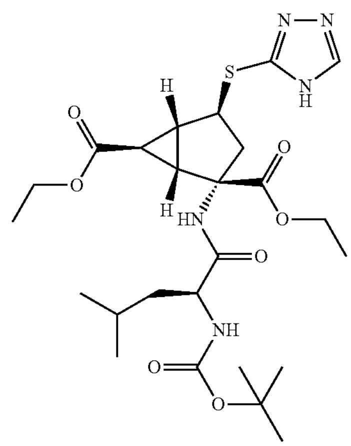 [SMILES: CCOC(=O)[C@H]1[C@H]2[C@@H]1[C@](NC(=O)[C@H](CC(C)C)NC(=O)OC(C)(C)C)(C(=O)OCC)C[C@@H]2Sc1nnc[nH]1] | 554 (M + 1), 576 (M + 23) |
| 24 | Diethyl (1R,2S,4S,5R,6R)-2-((S)-2-tert-butoxycarbonylamino-4-methylsulfanyl-butyrylamino)-4-(4H-[1,2,4]triazol-3-ylsulfanyl)-bicyclo[3.1.0]hexane-2,6-dicarboxylate | 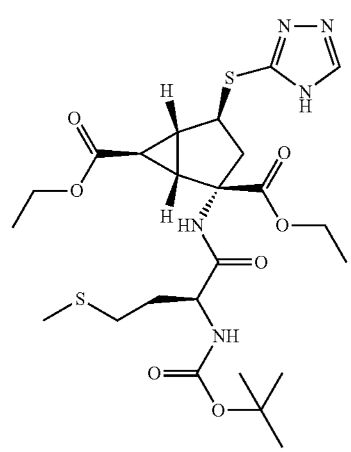 [SMILES: CCOC(=O)[C@H]1[C@H]2[C@@H]1[C@](NC(=O)[C@H](CCSC)NC(=O)OC(C)(C)C)(C(=O)OCC)C[C@@H]2Sc1nnc[nH]1] | 572 (M + 1), 594 (M + 23) |

Preparation 25

Diethyl(1R,2S,4R,5R,6R)-2-[2-((S)-tert-butoxycarbonylamino)-propionylamino]-4-(5-trifluoromethyl-1H-[1,2,4]triazol-3-ylsulfanyl)-bicyclo[3.1.0]hexane-2,6-dicarboxylate

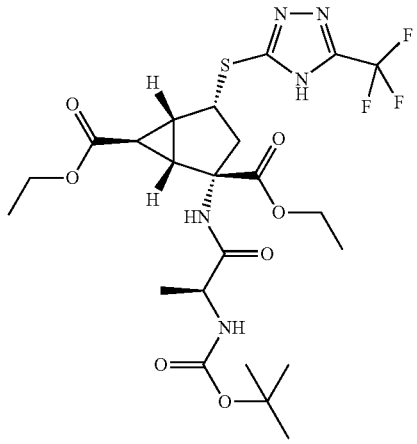 [SMILES: CCOC(=O)[C@H]1[C@H]2[C@@H]1[C@](NC(=O)[C@H](C)NC(=O)OC(C)(C)C)(C(=O)OCC)C[C@H]2Sc1nnc(C(F)(F)F)[nH]1]

Combine diethyl(1R,2S,4R,5R,6R)-2-amino-4-(5-trifluoromethyl-1H-[1,2,4]triazol-3-ylsulfanyl)-bicyclo[3.1.0]hexane-2,6-dicarboxylate hydrochloride (657 mg, 1.48 mmol), o-(7-azabenzotriazol-1-yl)-N,N,N',N'-tetramethyluronium hexafluorophosphate (730 mg, 1.92 mmol) and (2S)-2-(tert-butoxycarbonylamino)propanoic acid (363 mg, 1.92 mmol) in anhydrous dimethylformamide (12 mL) at room temperature, add diisopropylethylamine (3.0 mL, 17.20 mmol) and stir the mixture at room temperature overnight under a nitrogen atmosphere. Dilute the reaction mixture with ethyl acetate (60 mL) and wash with saturated sodium hydrogen carbonate solution (30 mL). Extract the aqueous phase with ethyl acetate. Combine organic phases, wash with water (30 mL) and brine (30 mL). Dry the organic phase over anhydrous sodium sulphate, filter and remove the solvent under vacuum. Purify by silica gel chromatography (110 g silica column) eluting with isohexane:ethyl acetate (95:5 to 10:90) to yield the title compound (321 mg, 38%). MS (m/z): 602 (M+23).

The following compounds in Table 5 are prepared essentially following method of preparation 25.

TABLE 5

| Prep No. | Chemical Name | Structure | Physical data MS (m/z) |
|---|---|---|---|
| 26 | Diethyl (1R,2S,4R,5R,6R)-2-[2-((S)-tert-butoxycarbonylamino)-4-methylsulfanyl-butyrylamino]-4-(5-trifluoromethyl-1H-[1,2,4]triazol-3-ylsulfanyl)-bicyclo[3.1.0]hexane-2,6-dicarboxylate | 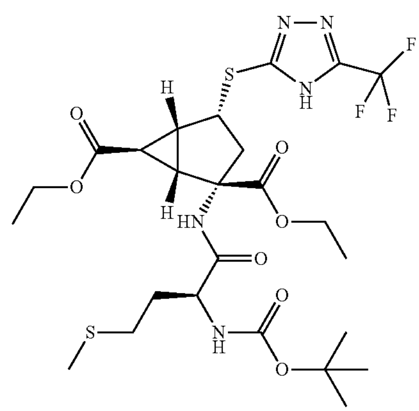 [SMILES: CCOC(=O)[C@H]1[C@H]2[C@@H]1[C@](NC(=O)[C@H](CCSC)NC(=O)OC(C)(C)C)(C(=O)OCC)C[C@H]2Sc1nnc(C(F)(F)F)[nH]1] | 662 (M + 23) |
| 27 | Diethyl (1R,2S,4R,5R,6R)-2-(2-tert-butoxycarbonylamino-acetylamino)-4-(5-trifluoromethyl-1H-[1,2,4]triazol-3-ylsulfanyl)-bicyclo[3.1.0]hexane-2,6-dicarboxylate | 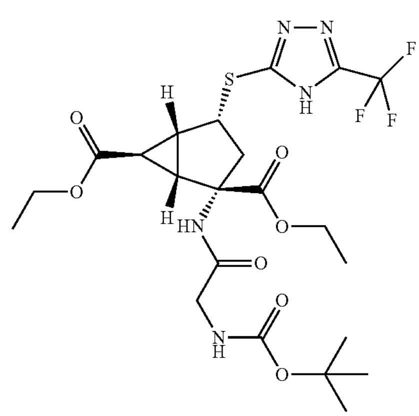 [SMILES: CCOC(=O)[C@H]1[C@H]2[C@@H]1[C@](NC(=O)CNC(=O)OC(C)(C)C)(C(=O)OCC)C[C@H]2Sc1nnc(C(F)(F)F)[nH]1] | 558 (M + 23) |

TABLE 5-continued

| Prep No. | Chemical Name | Structure | Physical data MS (m/z) |
|---|---|---|---|
| 28 | Diethyl (1R,2S,4R,5R,6R)-2-[2-((S)-tert-butoxycarbonylamino)-propionylamino]-4-(2H-[1,2,3]triazol-4-ylsulfanyl)-bicyclo[3.1.0]hexane-2,6-dicarboxylate | 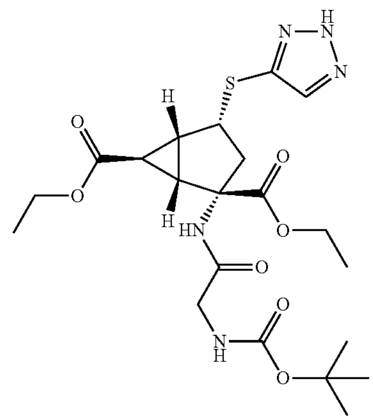 [SMILES: CCOC(=O)[C@H]1[C@H]2[C@@H]1[C@](NC(=O)CNC(=O)OC(C)(C)C)(C(=O)OCC)C[C@H]2Sc1cn[nH]n1] | 520 (M + 23) |
| 29 | Diethyl (1R,2S,4R,5R,6R)-2-[2-((S)-tert-butoxycarbonylamino)-propionylamino]-4-(2H-[1,2,3]triazol-4-ylsulfanyl)-bicyclo[3.1.0]hexane-2,6-dicarboxylate | 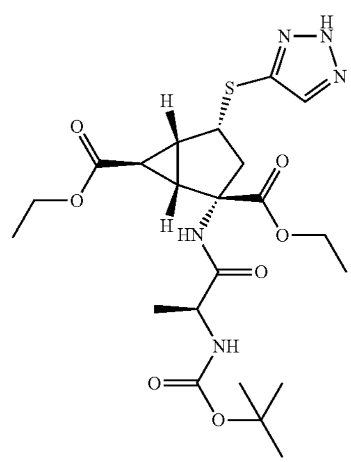 [SMILES: CCOC(=O)[C@H]1[C@H]2[C@@H]1[C@](NC(=O)[C@H](C)NC(=O)OC(C)(C)C)(C(=O)OCC)C[C@H]2Sc1cn[nH]n1] | 534 (M + 23) |
| 30 | Diethyl (1R,2S,4R,5R,6R)-2-[2-((S)-tert-butoxycarbonylamino)-4-methylsulfanyl-butyrylamino]-4-(2H-[1,2,3]triazol-4-ylsulfanyl)-bicyclo[3.1.0]hexane-2,6-dicarboxylate | 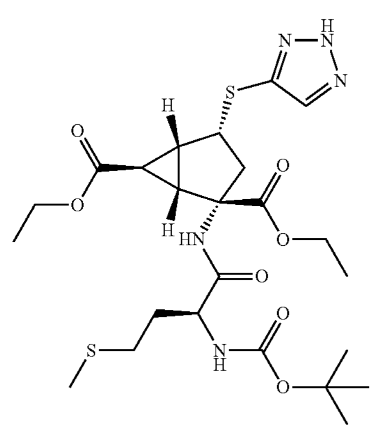 [SMILES: CCOC(=O)[C@H]1[C@H]2[C@@H]1[C@](NC(=O)[C@H](CCSC)NC(=O)OC(C)(C)C)(C(=O)OCC)C[C@H]2Sc1cn[nH]n1] | 572 (M + 1), 594 (M + 23) |

Preparation 31

Diethyl(1R,2S,4S,5R,6R)-2-(tert-butoxycarbonylamino)-4-(1H-1,2,4-triazol-3-ylsulfanyl)bicyclo[3.1.0]hexane-2,6-dicarboxylate

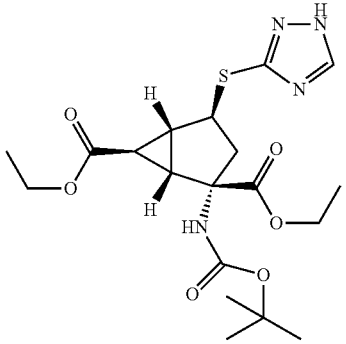 [SMILES: CCOC(=O)[C@H]1[C@H]2[C@@H]1[C@](NC(=O)OC(C)(C)C)(C(=O)OCC)C[C@@H]2Sc1nc[nH]n1]

To a suspension of diethyl(1R,2S,4S,5R,6R)-2-amino-4-(1H-[1,2,4]triazol-3-ylsulfanyl)-bicyclo[3.1.0]hexane-2,6-dicarboxylate hydrochloride (2.04 g, 5.41 mmol) in 1,4-dioxane (27.07 mL, 317.02 mmol) add ditert-butyldicarbonate (2.39 g, 10.83 mmol) and potassium carbonate (1.89 g, 13.53 mmol). Ten min later, add water (27.07 mL, 1.50 mol), and stir at room temperature for 2 days. Remove dioxane and dilute with ethyl acetate. Separate the layers and dry over magnesium sulfate, filter and concentrate. The title compound is obtained as a white solid (1.97 g, 83%). MS (m/z): 441 (M+1).

Preparation 32

(1R,2S,4S,5R,6R)-2-[[-2-(tert-butoxycarbonylamino)acetyl]amino]-4-(4H-1,2,4-triazol-3-ylsulfanyl)bicyclo[3.1.0]hexane-2,6-dicarboxylic acid

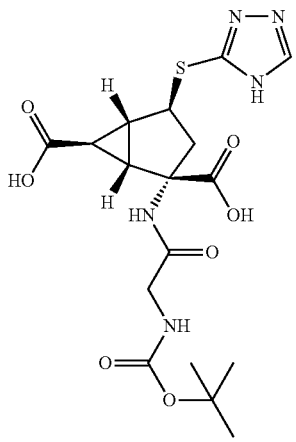 [SMILES: CC(C)(C)OC(=O)NCC(=O)N[C@@]1(C(=O)O)C[C@H](Sc2nnc[nH]2)[C@H]2[C@H](C(=O)O)[C@H]21]

Dissolve diethyl(1R,2S,4S,5R,6R)-2-[[-2-(tert-butoxycarbonylamino) acetyl]amino]-4-(4H-1,2,4-triazol-3-ylsulfanyl)bicyclo[3.1.0]hexane-2,6-dicarboxylate (0.420 g, 0.84 mmol) in tetrahydrofuran (7 mL) then add 2.5M lithium hydroxide (6.7 mL, 16.88 mmol). Stir the mixture at room temperature for 3.5 hours. Dilute the reaction mixture with water and wash with ethyl acetate. Discard the organic layer. Adjust the aqueous phase to pH=2 with 1N hydrochloric acid and extract with ethyl acetate. Dry the organic phase over magnesium sulfate, filter and concentrate to dryness to yield the title compound as a white solid (250 mg, 66%). MS (m/z): 442 (M+1), 464 (M+23).

The following compounds in Table 6 are prepared essentially following method of Preparation 32.

TABLE 6

| Prep No. | Chemical name | Structure | Physical data MS (m/z) |
|---|---|---|---|
| 33 | (1R,2S,4S,5R,6R)-2-((S)-2-tert-Butoxycarbonylamino-propionylamino)-4-(4H-[1,2,4]triazol-3-ylsulfanyl)-bicyclo[3.1.0]hexane-2,6-dicarboxylic acid | 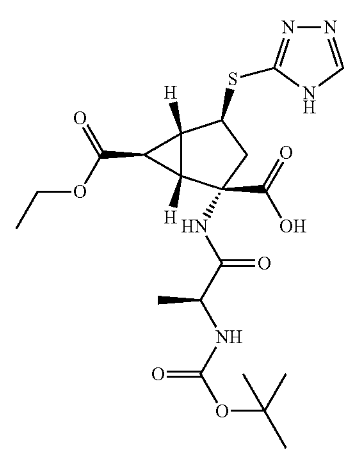 | 456 (M + 1) |

TABLE 6-continued

| Prep No. | Chemical name | Structure | Physical data MS (m/z) |
|---|---|---|---|
| 34 | (1R,2S,4S,5R,6R)-2-((S)-2-tert-Butoxy-carbonylamino-4-methyl-pentanoylamino)-4-(4H-[1,2,4]triazol-3-ylsulfanyl)-bicyclo[3.1.0]hexane-2,6-dicarboxylic acid | 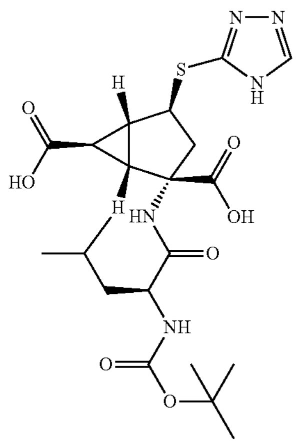 | 497 (M + 1) |
| 35 | (1R,2S,4S,5R,6R)-2-((S)-2-tert-Butoxy-carbonylamino-4-methylsulfanyl-butyrylamino)-4-(4H-[1,2,4]triazol-3-ylsulfanyl)-bicyclo[3.1.0]hexane-2,6-dicarboxylic acid | 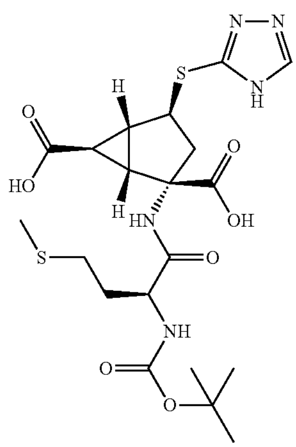 [SMILES: CSCC[C@H](NC(=O)OC(C)(C)C)C(=O)N[C@@]1(C(=O)O)C[C@H](Sc2nnc[nH]2)[C@H]2[C@H](C(=O)O)[C@H]21] | 516 (M + 1) |
| 36 | (1R,2S,4R,5R,6R)-2-[2-((S)-tert-Butoxycarbonylamino)-propionylamino]-4-(5-trifluoromethyl-1H-[1,2,4]triazol-3-ylsulfanyl)-bicyclo[3.1.0]hexane-2,6-dicarboxylic acid[3] | 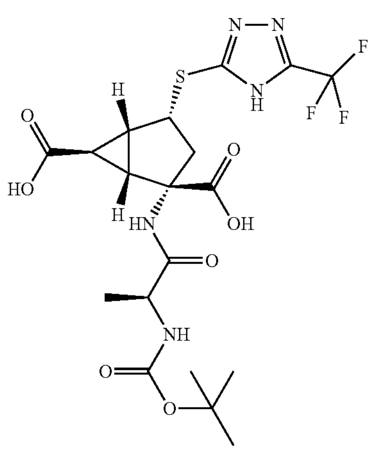 [SMILES: C[C@H](NC(=O)OC(C)(C)C)C(=O)N[C@@]1(C(=O)O)C[C@@H](Sc2nnc(C(F)(F)F)[nH]2)[C@H]2[C@H](C(=O)O)[C@H]21] | 546 (M + 23) |

TABLE 6-continued

| Prep No. | Chemical name | Structure | Physical data MS (m/z) |
|---|---|---|---|
| 37 | (1R,2S,4R,5R,6R)-2-[2-((S)-tert-Butoxycarbonylamino)-4-methylsulfanyl-butyrylamino]-(5-trifluoromethyl-1H-[1,2,4]triazol-3-ylsulfanyl)-bicyclo[3.1.0]hexane-2,6-dicarboxylic acid[3] | 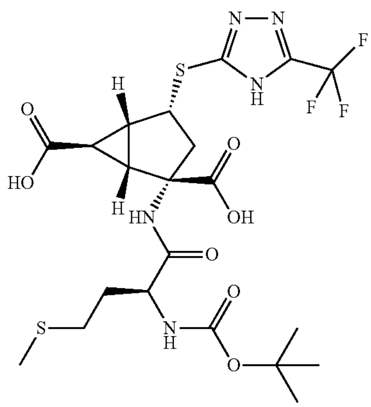 [SMILES: CSCC[C@H](NC(=O)OC(C)(C)C)C(=O)N[C@@]1(C(=O)O)C[C@@H](Sc2nnc(C(F)(F)F)[nH]2)[C@H]2[C@H](C(=O)O)[C@H]21] | 584 (M + 1) |
| 38 | (1R,2S,4R,5R,6R)-2-(2-tert-Butoxycarbonylamino-acetylamino)-4-(5-trifluoromethyl-1H-[1,2,4]triazol-3-ylsulfanyl)-bicyclo[3.1.0]hexane-2,6-dicarboxylic acid[3] | 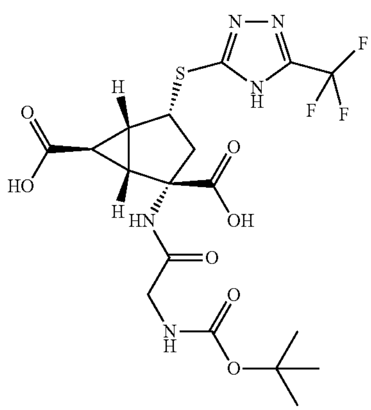 [SMILES: CC(C)(C)OC(=O)NCC(=O)N[C@@]1(C(=O)O)C[C@@H](Sc2nnc(C(F)(F)F)[nH]2)[C@H]2[C@H](C(=O)O)[C@H]21] | 510 (M + 1), 532 (M + 23) |
| 39 | (1R,2S,4R,5R,6R)-2-(2-tert-Butoxycarbonylamino-acetylamino)-4-(2H-[1,2,3]triazol-4-ylsulfanyl)-bicyclo[3.1.0]hexane-2,6-dicarboxylic acid[3] | 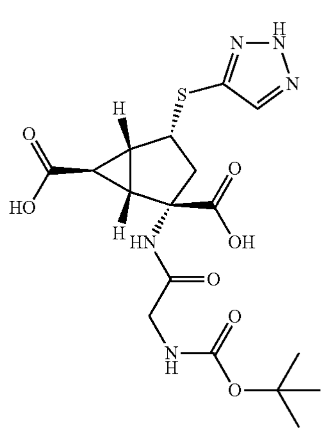 [SMILES: CC(C)(C)OC(=O)NCC(=O)N[C@@]1(C(=O)O)C[C@@H](Sc2cn[nH]n2)[C@H]2[C@H](C(=O)O)[C@H]21] | 442 (M + 1), 464 (M + 23) |

TABLE 6-continued

| Prep No. | Chemical name | Structure | Physical data MS (m/z) |
|---|---|---|---|
| 40 | (1R,2S,4R,5R,6R)-2-[2-((S)-tert-Butoxycarbonylamino)-propionylamino]-4-(2H-[1,2,3]triazol-4-ylsulfanyl)-bicyclo[3.1.0]hexane-2,6-dicarboxylic acid[3] | 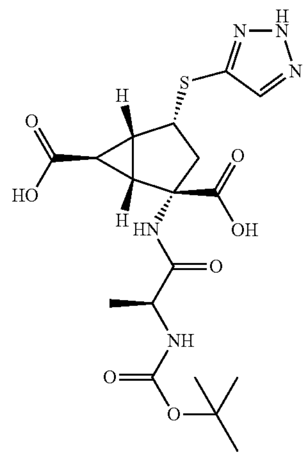 [SMILES: C[C@H](NC(=O)OC(C)(C)C)C(=O)N[C@@]1(C(=O)O)C[C@@H](Sc2cn[nH]n2)[C@H]2[C@H](C(=O)O)[C@H]21] | 456 (M + 1), 478 (M + 23) |
| 41 | (1R,2S,4R,5R,6R)-2-[2-((S)-tert-Butoxycarbonylamino)-4-methylsulfanyl-butyrylamino]-4-(2H-[1,2,3]triazol-4-ylsulfanyl)-bicyclo[3.1.0]hexane-2,6-dicarboxylic acid[3] | 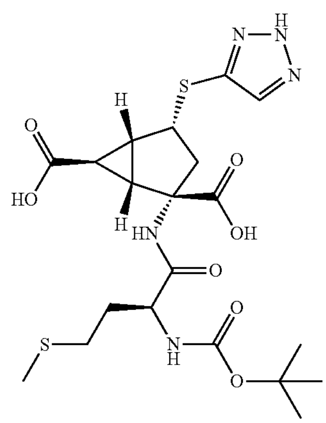 [SMILES: CSCC[C@H](NC(=O)OC(C)(C)C)C(=O)N[C@@]1(C(=O)O)C[C@@H](Sc2cn[nH]n2)[C@H]2[C@H](C(=O)O)[C@H]21] | 516 (M + 1), |

[3]The base used in the reaction is 2.0M LiOH.

Preparation 42

(1R,2S,4S,5R,6R)-2-tert-Butoxycarbonylamino-4-(1H-[1,2,4]triazol-3-ylsulfanyl)-bicyclo[3.1.0]hexane-2,6-dicarboxylic acid

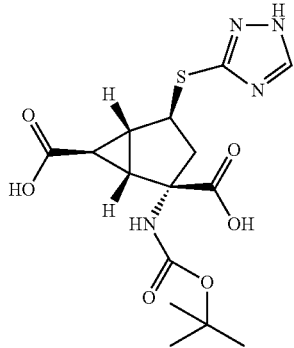 [SMILES: CC(C)(C)OC(=O)N[C@@]1(C(=O)O)C[C@H](Sc2nc[nH]n2)[C@H]2[C@H](C(=O)O)[C@H]21]

To diethyl(1R,2S,4S,5R,6R)-2-tert-butoxycarbonylamino-4-(1H-[1,2,4]triazol-3-ylsulfanyl)-bicyclo[3.1.0]hexane-2,6-dicarboxylate (1.9 g, 4.31 mmol) in tetrahydrofuran (20 mL) add 2.5M aqueous solution lithium hydroxide (20.70 mL, 51.76 mmol) and stir at room temperature overnight. Evaporate the tetrahydrofuran. Dilute with water and wash with ethyl acetate. Discard the organic layer. Adjust aqueous phase to pH=2 with 5M hydrochloric acid and extract with ethyl acetate. Separate the layers and dry the organics over magnesium sulfate, filter and concentrate. The title compound is obtained as a white solid (1.58 g, 95%). MS (m/z): 385 (M+1).

Preparation 43

(1S,2S,5R,6R)-2-(tert-Butoxycarbonylamino)-4-oxo-bicyclo[3.1.0]hexane-2,6-dicarboxylic acid

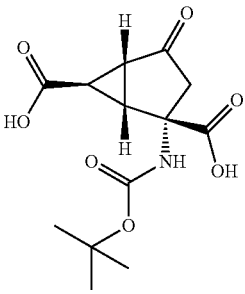 [SMILES: CC(C)(C)OC(=O)N[C@@]1(C(=O)O)CC(=O)[C@H]2[C@H](C(=O)O)[C@H]21]

Add 2.5M sodium hydroxide (15.55 mL, 38.88 mmol) to a stirred solution of the ditert-butyl(1S,2S,5R,6R)-2-(tert-butoxycarbonylamino)-4-oxo-bicyclo[3.1.0]hexane-2,6-dicarboxylate (2.0 g, 4.86 mmol) in tetrahydrofuran (24.3 mL) and ethanol (9.72 mL). Heat the reaction mixture to 60° C. and maintain stirring overnight. Continue heating for 4 hours then wash with ethyl acetate. Cool the aqueous phase in an ice bath and acidify to pH=2-3 with 1N hydrochloric acid solution. Extract with ethyl acetate (3 times), dry the organic on sodium sulfate, filter and concentrate to give the title compound as an orange solid (1.4 g, 96%). MS (m/z): 322 (M+23).

Preparation 44

Dibenzyl(1S,2S,5R,6R)-2-tert-butoxycarbonylamino-4-oxo-bicyclo[3.1.0]hexane-2,6-dicarboxylate

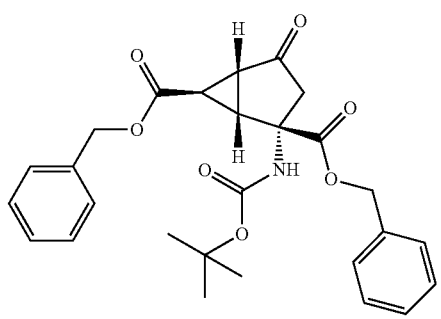 [SMILES: CC(C)(C)OC(=O)N[C@@]1(C(=O)OCc2ccccc2)CC(=O)[C@H]2[C@H](C(=O)OCc3ccccc3)[C@H]21]

Add benzyl bromide (8.69 mL, 72.9 mmol) dropwise to a stirred suspension of (1S,2S,5R,6R)-2-(tert-butoxycarbonylamino)-4-oxo-bicyclo[3.1.0]hexane-2,6-dicarboxylic acid (7.27 g, 24.3 mmol) and cesium carbonate (15.83 g, 48.6 mmol) in dry N,N-dimethylformamide (60 mL). Stir the resulting mixture at room temperature overnight under nitrogen. Quench with water and dilute with ethyl acetate. Extract the aqueous phase with ethyl acetate (3 times) and wash the organic layers with brine and water. Dry over sodium sulfate, filter and concentrate to give the crude material as a pale brown oil. Purify by flash chromatography eluting with ethyl acetate:hexane (20:80 to 30:70) to give the title compound as gummy yellow foam (9.15 g, 78.5%). MS (m/z): 502 (M+23).

Preparation 45

Dibenzyl(1S,2S,4S,5R,6R)-2-tert-butoxycarbonylamino-4-hydroxy-bicyclo[3.1.0]hexane-2,6-dicarboxylate

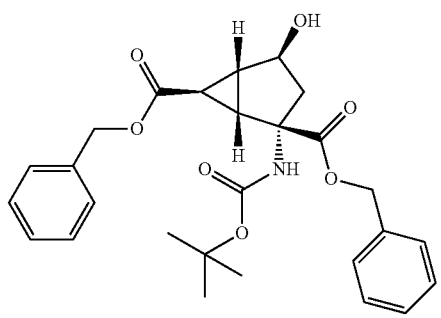 [SMILES: CC(C)(C)OC(=O)N[C@@]1(C(=O)OCc2ccccc2)C[C@H](O)[C@H]2[C@H](C(=O)OCc3ccccc3)[C@H]21]

Add 1M L-selectride solution in THF (30 mL, 30 mmol) dropwise to a stirred solution of bis[(phenyl)methyl](1S,2S,5R,6R)-2-(tert-butoxycarbonylamino)-4-oxo-bicyclo[3.1.0]hexane-2,6-dicarboxylate (9.15 g, 19.08 mmol) in tetrahydrofuran (20 mL) at −78° C. Stir the resulting orange mixture under nitrogen for 1 hour 45 minutes. Quench with a saturated solution of sodium hydrogen carbonate at −78° C. Dilute with water and ethyl acetate. Separate the layers and wash the organic phase with brine and water. Dry over sodium sulfate, filter and concentrate to dryness to give the crude material as pale yellow oil. Purify the combined material by flash chromatography eluting with ethyl acetate:hexanes (20:80 to 50:50) to give the title product as a single isomer (9.19 g, 100%). MS (m/z): 504 (M+23)

Preparation 46

Dibenzyl(1S,2S,4S,5R,6R)-2-tert-butoxycarbonylamino-4-(toluene-4-sulfonyloxy)-bicyclo[3.1.0]hexane-2,6-dicarboxylate

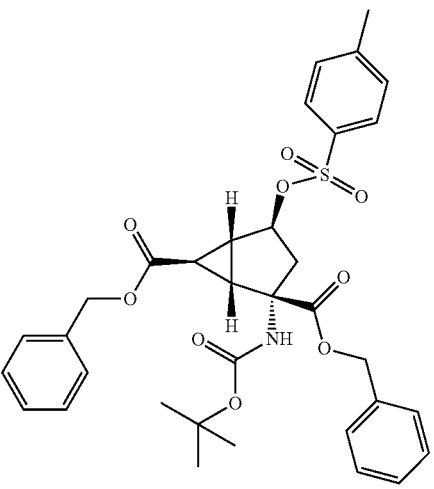 [SMILES: Cc1ccc(S(=O)(=O)O[C@H]2C[C@@](NC(=O)OC(C)(C)C)(C(=O)OCc3ccccc3)[C@@H]3[C@@H](C(=O)OCc4ccccc4)[C@@H]32)cc1]

The title product is prepared essentially according to the method of Preparation 1 (75% yield). MS (m/z): 658 (M+23).

Preparation 47

Dibenzyl(1R,2S,4R,5R,6R)-2-tert-butoxycarbonylamino-4-(1H-[1,2,3]triazol-4-ylsulfanyl)-bicyclo[3.1.0]hexane-2,6-dicarboxylate

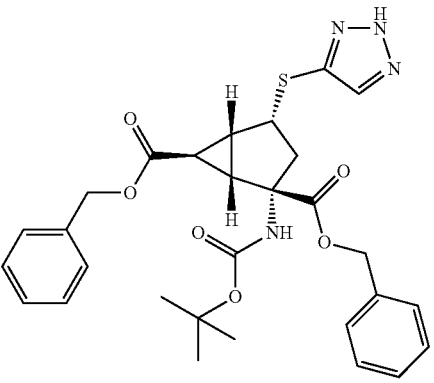 [SMILES: CC(C)(C)OC(=O)N[C@@]1(C(=O)OCc2ccccc2)C[C@@H](Sc2cn[nH]n2)[C@H]2[C@H](C(=O)OCc3ccccc3)[C@H]21]

Add 1H-5-Mercapto-1,2,3-triazole, sodium salt dihydrate (0.174 g, 1.42 mmol) to s stirred solution of (1S,2S,4S,5R,6R)-2-(tert-butoxycarbonylamino)-4-(tosyloxy)bicyclo[3.1.0]hexane-2,6-dicarboxylic acid dibenzyl ester (0.6 g, 0 943 mmol) and in anhydrous dimethylformamide (8 mL) and heat at 70° C. overnight. Dilute reaction mixture with ethyl acetate (60 mL) and wash organic layer with NaHCO$_3$ (30 mL) and brine (30 mL), dry over anhydrous Na$_2$SO$_4$), concentrate, and purify via silica gel chromatography (40 g silica column) eluting with 0-60% ethyl acetate in isohexane to give the title compound as a colorless gum (0.405 g, 76% yield). MS (m/z): 587 (M+23)

Preparation 48

Bis-(4-methoxy-benzyl)-(1R,2S,4S,5R,6R)-2-tert-butoxycarbonylamino-4-(1H-[1,2,4]triazol-3-ylsulfanyl)-bicyclo[3.1.0]hexane-2,6-dicarboxylate

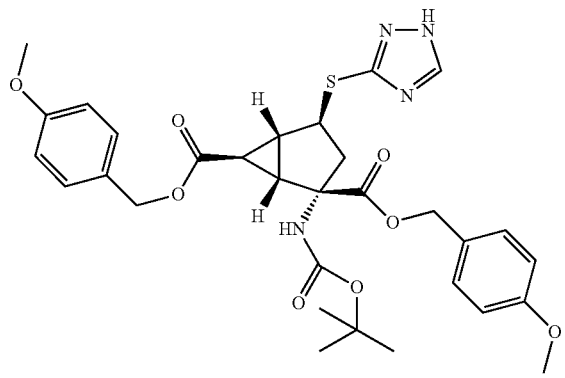 [SMILES: COc1ccc(COC(=O)[C@H]2[C@H]3[C@@H]2[C@](NC(=O)OC(C)(C)C)(C(=O)OCc2ccc(OC)cc2)C[C@@H]3Sc2nc[nH]n2)cc1]

Stir a suspension of (1R,2S,4S,5R,6R)-2-tert-butoxycarbonylamino-4-(1H-[1,2,4]triazol-3-ylsulfanyl)-bicyclo[3.1.0]hexane-2,6-dicarboxylic acid (369 mg, 0.959 mmol), O-(7-azabenzotriazol-1-yl)-N,N,N',N'-tetramethyluronium hexafluorophosphate (0.985 g, 2.59 mmol), diisopropylethylamine (0.920 mL), in dichloromethane (9.60 mL) for 15 min. Then, add benzenemethanol, 4-methoxy (0.365 g, 2.59 mmol) and stir at room temperature overnight. Remove the solvent and purify via silica gel chromatography (12 g silica gel cartridge) eluting with dichloromethane/methanol gradient to provide the title compound (240 mg, 40%). MS (m/z): 625 (M+1).

The following compound in Table 7 is prepared essentially following the method of Preparation 48.

TABLE 7

| Prep. No | Chemical name | Structure | Phyiscal data MS m/z |
|---|---|---|---|
| 49 | bis[[3-(trifluoromethyl)phenyl]methyl] (1R,2S,4S,5R,6R)-2-(tert-butoxycarbonylamino)-4-(1H-1,2,4-triazol-3-ylsulfanyl)bicyclo[3.1.0]hexane 2,6-dicarboxylate | 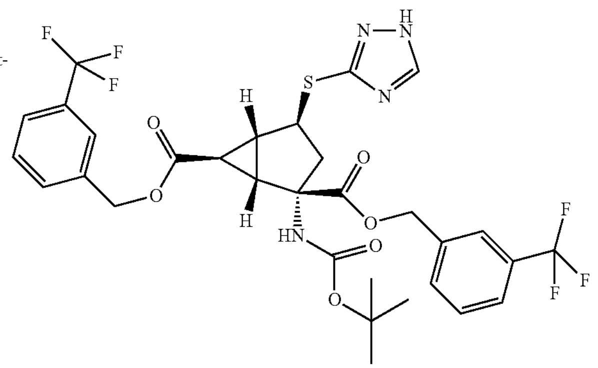 | 701 (M + 1) |

Preparation 50

Bis(2,2-dimethylpropanoyloxymethyl)(1R,2S,4S,5R,6R)-2-(tert-butoxycarbonylamino)-4-(1H-1,2,4-triazol-3-ylsulfanyl)bicyclo[3.1.0]hexane-2,6-dicarboxylate

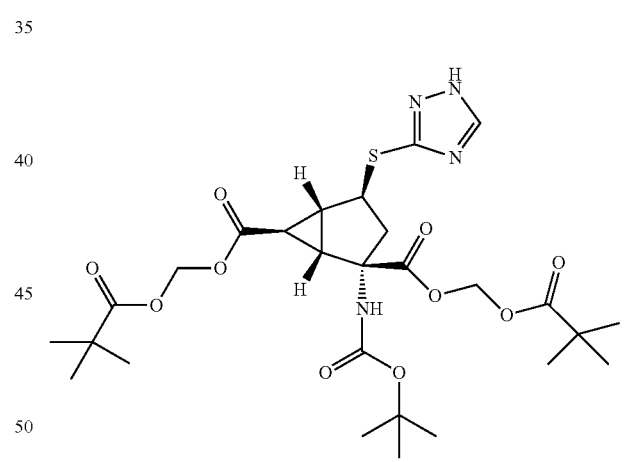

Add sodium bicarbonate (0.393 g, 4.68 mmol), sodium iodide (0.351 g, 2.34 mmol) and propanoic acid, 2,2-dimethyl-chloromethyl ester (352.60 mg, 2.34 mmol) to a solution of (1R,2S,4S,5R,6R)-2-tert-butoxycarbonylamino-4-(1H-[1,2,4]triazol-3-ylsulfanyl)bicyclo[3.1.0]hexane-2,6-dicarboxylic acid (0.300 g, 0.780 mmol) in 3 mL of dry dimethylformamide. Stir the resulting heterogeneous mixture for 18 h. Remove the solvent under vacuum, add water and extract with ethyl acetate. Separate the layers and dry the organics over magnesium sulfate, filter and concentrate. Purify the crude product through a 5 g Phenomenex STRATA™ normal phase cartridge eluting with a 50% hexane:ethyl acetate mixture to provide the title compound (96 mg, 20%). MS (m/z): 613 (M+1).

Preparation 51

2-tert-Butyl-6-ethyl(1R,2S,4S,5R,6R)-2-amino-4-(1H-[1,2,4]triazol-3-ylsulfanyl)-bicyclo[3.1.0]hexane-2,6-dicarboxylate hydrochloride

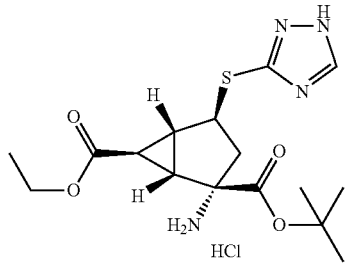 [SMILES: CCOC(=O)[C@H]1[C@H]2[C@@H]1[C@](N)(C(=O)OC(C)(C)C)C[C@@H]2Sc1nc[nH]n1 ; Cl]

Add acetyl chloride (1.12 mL, 15.71 mmol) dropwise to a solution of ditert-butyl(1R,2S,4S,5R,6R)-2-(tert-butoxycarbonylamino)-4-(1H-1,2,4-triazol-3-ylsulfanyl)bicyclo[3.1.0]hexane-4,6-dicarboxylate (1.3 g, 2.62 mmol) in ethanol (9.14 mL). Heat the mixture in a sealed tube at 50° C. for 2 hours. Remove solvent to provide the title compound (950 mg, 90%). MS (m/z): 369 (M+1).

Preparation 52

(1R,2S,4S,5R,6R)-4-amino-6-ethoxycarbonyl-2-(1H-1,2,4-triazol-3-ylsulfanyl)bicyclo[3.1.0]hexane-4-carboxylic acid hydrochloride

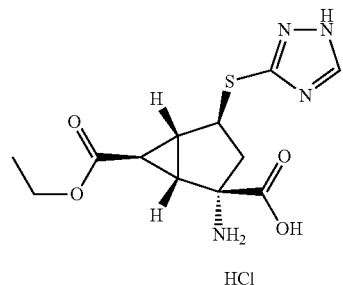 [SMILES: CCOC(=O)[C@H]1[C@H]2[C@@H]1[C@](N)(C(=O)O)C[C@@H]2Sc1nc[nH]n1 ; Cl]

Dissolve 2-tert-butyl-6-ethyl(1R,2S,4S,5R,6R)-2-amino-4-(1H-[1,2,4]triazol-3-ylsulfanyl)-bicyclo[3.1.0]hexane-2,6-dicarboxylate hydrochloride (946 mg, 2.34 mmol) in a saturated solution of hydrogen chloride gas in ethyl acetate (8 mL) and stir at room temperature for 25 hours. Remove solvent to provide the title compound (831 mg, 101%). MS (m/z): 313 (M+1)

Preparation 53

(1R,2S,4S,5R,6R)-2-(tert-butoxycarbonylamino)-6-ethoxycarbonyl-4-(1H-1,2,4-triazol-3-ylsulfanyl)bicyclo[3.1.0]hexane-2-carboxylic acid

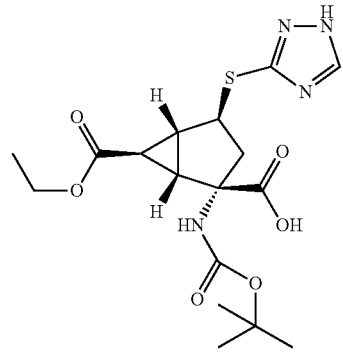 [SMILES: CCOC(=O)[C@H]1[C@H]2[C@@H]1[C@](NC(=O)OC(C)(C)C)(C(=O)O)C[C@@H]2Sc1nc[nH]n1]

Add ditert-butyldicarbonate (935.39 mg, 4.24 mmol) and potassium carbonate (888.5 mg, 6.36 mmol) to a suspension of (1R,2S,4S,5R,6R)-4-amino-6-ethoxycarbonyl-2-(1H-1,2,4-triazol-3-ylsulfanyl)bicyclo[3.1.0]hexane-4-carboxylic acid hydrochloride (740 mg, 2.12 mmol) in 1,4-dioxane (10.61 mL). Stir mixture at room temperature. Ten min later, add water (10.61 mL) and stir at room temperature for 2 days. Remove the dioxane and dilute with ethyl acetate, adjust pH acidic with 5M HCl. Separate the layers and dry the organics over magnesium sulfate, filter and concentrate to provide the title compound (270 mg, 31%). MS (m/z): 413 (M+1)

Preparation 54

2-Benzyl-6-ethyl(1R,2S,4S,5R,6R)-2-tert-butoxycarbonylamino-4-(1H-[1,2,4]triazol-3-ylsulfanyl)-bicyclo[3.1.0]hexane-2,6-dicarboxylate

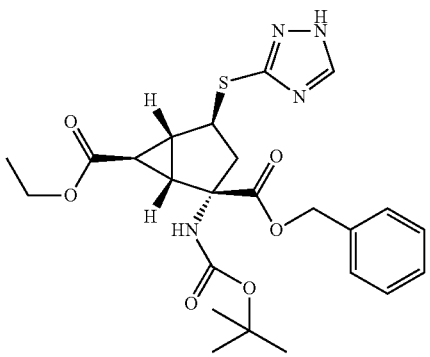 [SMILES: CCOC(=O)[C@H]1[C@H]2[C@@H]1[C@](NC(=O)OC(C)(C)C)(C(=O)OCc1ccccc1)C[C@@H]2Sc1nc[nH]n1]

Stir a suspension of (1R,2S,4S,5R,6R)-2-(tert-butoxycarbonylamino)-6-ethoxycarbonyl-4-(1H-1,2,4-triazol-3-ylsulfanyl)bicyclo[3.1.0]hexane-2-carboxylic acid (270 mg, 0.654 mmol), O-(7-Azabenzotriazol-1-yl)-N,N,N',N'-tetramethyluronium Hexafluorophosphate (0.373 g, 0.982 mmol), diisopropylethylamine (0.342 mL, 1.96 mmol), in dichloromethane (6.55 mL) for 15 minutes at room temperature and add benzyl alcohol (0.101 mL, 0.982 mmol). Stir at room temperature overnight. Remove the solvent and purify first via silica column chromatography (4 g silica gel cartridge, eluent dichloromethane/methanol gradient (desired compound elute with 6% of methanol), and second via Waters OASIS® HLB cartridge eluting with 3:1 acetonitrile/water. The title compound is obtained as a white solid (100 mg, 30%). MS (m/z): 503 (M+1).

Example 1

(1R,2S,4R,5R,6R)-2-Amino-4-(2H-[1,2,3]triazol-4-ylsulfanyl)-bicyclo[3.1.0]hexane-2,6-dicarboxylic acid hydrochloride

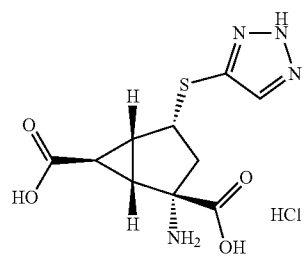 [SMILES: N[C@@]1(C(=O)O)C[C@@H](Sc2cn[nH]n2)[C@H]2[C@H](C(=O)O)[C@H]21 ; Cl]

Add zinc dibromide (0.88 g, 3.91 mmol) to a stirring solution of ditert-butyl(1R,2S,4R,5R,6R)-2-tert-butoxycarbonylamino-4-(2H-[1,2,3]triazol-4-ylsulfanyl)-bicyclo[3.1.0]hexane-2,6-dicarboxylate (194 mg, 0.39 mmol) in dichloromethane (30 mL). Stir overnight at 50° C. Add more zinc dibromide (0.44 g, 1.95 mmol) and continue to stir at 50° C. until starting material is completely consumed. Evaporate solvent and stir residue in 2M aqueous hydrochloric acid (5 mL) at 50° C. until only desired product is present. Cool reaction mixture and purify the residue by cation-exchange chromatography (DOWEX® 50WX8-100). Allow the compound to flow through the column at a drip rate of about 1 drop every 1-2 seconds. After the initial loading volume has dropped to the resin surface, rinse with water (5 to 10 mL) and repeat 3 times. Monitor the pH of the effluent and continue rinsing with water until application complete (pH cycle observed: effluent from the column initially at pH=7 then drop to pH=1 and return back to pH=7). Wash the column with at least one column volume each of water, water:tetrahydrofuran (1:1) then water. Displace the product from the resin with 10% pyridine:water. Continue to elute with 10% pyridine:water until no additional product is detected. Concentrate the fractions containing the product to obtain a colorless solid. Dry the solid. Dissolve in 2M hydrochloric acid and evaporate to provide the title compound as a white solid (94 mg, 75%). MS (m/z): 285 (M+1).

The following compounds in Table 8 are prepared essentially following method of Example 1.

TABLE 8

| Ex No | Chemical name | Structure | Physical data MS (m/z) |
|---|---|---|---|
| 2 | (1R,2S,4R,5R,6R)-2-Amino-4-(5-trifluoromethyl-1H-[1,2,4]triazol-3-ylsulfanyl)-bicyclo[3.1.0]hexane-2,6-dicarboxylic acid hydrochloride | 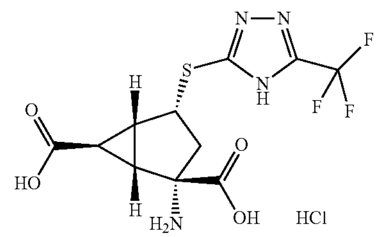 [SMILES: N[C@@]1(C(=O)O)C[C@@H](Sc2nnc(C(F)(F)F)[nH]2)[C@H]2[C@H](C(=O)O)[C@H]21 ; Cl] | 353 (M + 1) |
| 3 | (1R,2S,4R,5R,6R)-2-Amino-4-(5-amino-[1,3,4]triazol-2-ylsulfanyl)-bicyclo[3.1.0]hexane-2,6-dicarboxylic acid[4] | 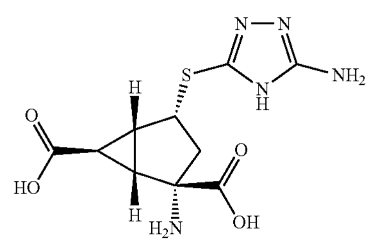 [SMILES: Nc1nnc(S[C@@H]2C[C@@](N)(C(=O)O)[C@@H]3[C@@H](C(=O)O)[C@@H]32)[nH]1] | 300 (M + 1) |
| 4 | (1R,2S,4S,5R,6R)-2-Amino-4-[(5-methyl-4H-1,2,4-triazol-3-yl)sulfanyl]bicyclo[3.1.0]hexane-2,6-dicarboxylic acid[4] | 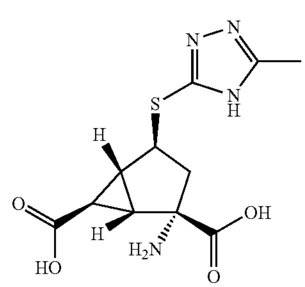 [SMILES: Cc1nnc(S[C@H]2C[C@@](N)(C(=O)O)[C@@H]3[C@@H](C(=O)O)[C@@H]32)[nH]1] | 299 (M + 1) |
| 5 | (1R,2S,4S,5R,6R)-2-Amino-4-(5-amino-1H-[1,2,4]triazol-3-ylsulfanyl)-bicyclo[3.1.0]hexane-2,6-dicarboxylic acid hydrochloride | 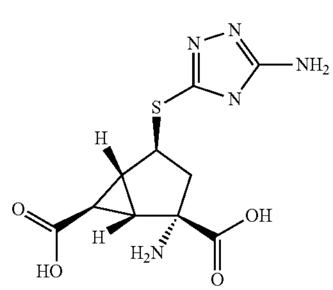 [SMILES: Nc1nnc(S[C@H]2C[C@@](N)(C(=O)O)[C@@H]3[C@@H](C(=O)O)[C@@H]32)[nH]1] | 300 (M + 1). |

TABLE 8-continued

| Ex No | Chemical name | Structure | Physical data MS (m/z) |
|---|---|---|---|
| 6 | (1R,2S,4S,5R,6R)-2-Amino-4-[(5-isopropyl-4H-1,2,4-triazol-3-yl)sulfanyl]bicyclo[3.1.0]hexane-2,6- dicarboxylic acid hydrochloride | 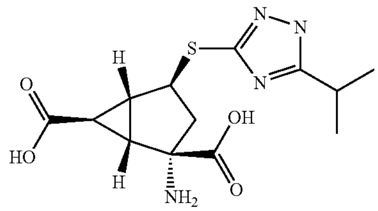 | 327 (M + 1). |
| 7 | (1R,2S,4S,5R,6R)-2-Amino-4-[(5-cyclopropyl-4H-1,2,4-triazol-3-yl)sulfanyl]bicyclo[3.1.0]hexane-2,6- dicarboxylic acid[4] | 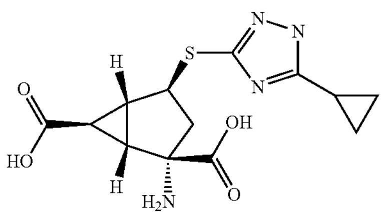 [SMILES: N[C@@]1(C(=O)O)C[C@H](Sc2n[nH]c(C3CC3)n2)[C@H]2[C@H](C(=O)O)[C@H]21] | 325 (M + 1) |

[4]Final compounds are isolated directly from cation-exchange chromatography and concentrated to dryness.

Example 8

(1R,2S,4R,5R,6R)-2-Amino-4-(5-difluoromethyl-1H-[1,2,4]triazol-3-ylsulfanyl)-bicyclo[3.1.0]hexane-2,6-dicarboxylic acid hydrochloride

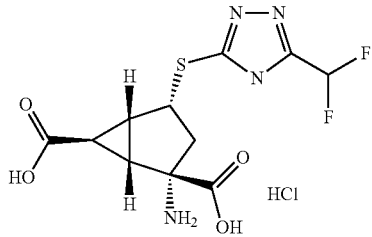 [SMILES: N[C@@]1(C(=O)O)C[C@@H](Sc2nnc(C(F)F)[nH]2)[C@H]2[C@H](C(=O)O)[C@H]21 ; Cl]

Add ditert-butyl(1R,2S,4R,5R,6R)-2-(tert-butoxycarbonylamino)-4-[[5-(difluoromethyl)-4H-1,2,4-triazol-3-yl]sulfanyl]bicyclo[3.1.0]hexane-2,6-dicarboxylate (0.356 g, 651.3 µmol) in 1,4-dioxane (1.63 mL) to a solution of hydrogen chloride (4M in dioxane). Heat the mixture to 50° C. with stirring. A solid precipitate out of solution soon after heating commenced. Cool the reaction mixture and concentrate under reduced pressure. Purify the residue by silica gel chromatography (40 g SiO$_2$) eluting with 0-20% hydrochloric acid (0.01 M aqueous) in acetonitrile gradient over 60 minutes at 40 mL/minute flow rate. Concentrate under reduced pressure to provide the crude material as oil. Re-purify using same conditions. Concentrate under reduced pressure to give the title compound as a white solid (0.196 g, 93%). MS (m/z): 335 (M+1).

The following compound in Table 9 is prepared essentially following method of Example 8.

TABLE 9

| Ex No | Chemical name | Structure | Physical data MS (m/z) |
|---|---|---|---|
| 9 | (1R,2S,4S,5R,6R)-2-amino-4-{[5-(difluoromethyl)-4H-1,2,4-triazol-3-yl]sulfanyl}bicyclo[3.1.0]hexane-2,6-dicarboxylic acid hydrochloride | 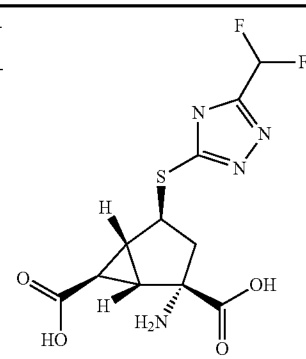 | 335 (M + 1) |

Example 10

(1R,2S,4S,5R,6R)-2-amino-4-(1H-1,2,4-triazol-3-ylsulfanyl)bicyclo[3.1.0]hexane-2,6-dicarboxylic acid

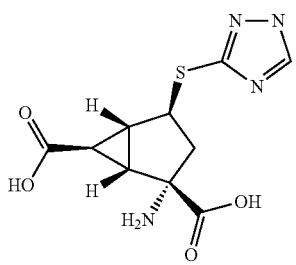 [SMILES: N[C@@]1(C(=O)O)C[C@H](Sc2nc[nH]n2)[C@H]2[C@H](C(=O)O)[C@H]21]

Add 4M hydrogen chloride in 1,4-dioxane (20 mL) to a solution of ditert-butyl(1R,2S,4S,5R,6R)-2-tert-butoxycarbonylamino-4-(1H-[1,2,4]triazol-3-ylsulfanyl)-bicyclo[3.1.0]hexane-2,6-dicarboxylate (1.64 g, 3.30 mmol) in 1,4-dioxane (20 mL) and shake mixture at 50° C. overnight. Concentrate to dryness. Purify by cationic ion exchange (DOWEX® Marathon C, Na⁺ Form strongly acidic). Dissolve the residue in a minimum amount of water to solubilize the material and load onto the resin. Wash the resin successively with 2 column volume of water, then 2 column volume of water: tetrahydrofuran (1:1) and 2 column volumes of water. Elute the desired product with 2 column volumes of 10% pyridine in water to give the title compound as a white solid. MS (m/z): 285 (M+1). 1H NMR (300 MHz, $D_2O$): 4.25 (d, J=7.3 Hz, 1H), 2.53-2.38 (m, 3H), 2.23 (dd, J=8.1, 16.1 Hz, 1H), 1.95 (t, J=3.3 Hz, 1H).

The following compounds in Table 10 are prepared essentially following method of Example 10.

Example 13

(1R,2S,4R,5R,6R)-2-amino-4-[(5-methyl-4H-1,2,4-triazol-3-yl)sulfanyl]bicyclo[3.1.0]hexane-2,6-dicarboxylic acid

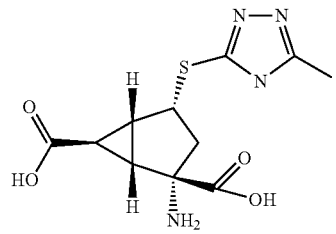

Dissolve ditert-butyl(1R,2S,4R,5R,6R)-2-(tert-butoxycarbonylamino)-4-[(5-methyl-4H-1,2,4-triazol-3-yl)sulfanyl]bicyclo[3.1.0]hexane-2,6-dicarboxylate (85 mg, 0.166 mmol) acetic acid (1 mL) and water (1 mL). Heat the mixture to 160° C. at approximately 40 Watts in a BIOTAGE® Initiator microwave for 6 minutes. Concentrate reaction mixture under reduced pressure. Add water and remove under reduced pressure twice to remove excess acetic acid to give the title compound as a white solid (40 mg, 88.6%). MS (m/z): 299 (M+1).

The following compounds in Table 11 are prepared essentially following method of Example 13.

TABLE 10

| Ex No | Chemical name | Structure | Physical data MS (m/z) |
|---|---|---|---|
| 11 | (1R,2S,4S,5R,6R)-2-Amino-4-(1H-triazol-4-ylsulfanyl)bicyclo[3.1.0]hexane-2,6-dicarboxylic acid hydrochloride[5] | 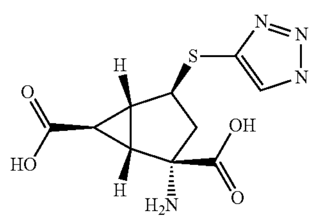 [SMILES: N[C@@]1(C(=O)O)C[C@H](Sc2c[nH]nn2)[C@H]2[C@H](C(=O)O)[C@H]21] | 285 (M + 1) |
| 12 | (1R,2S,4S,5R,6R)-2-Amino-4-[[5-(trifluoromethyl)-1H-1,2,4-triazol-3-yl]sulfanyl]bicyclo[3.1.0]hexane-2,6-dicarboxylic acid hydrochloride[5] | 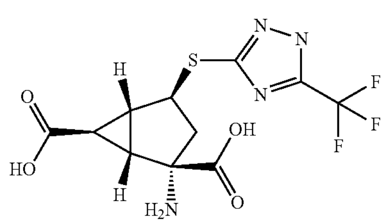 | 353 (M + 1) |

[5]Add 2M HCl to the resulting solution and concentrate under reduced pressure.

TABLE 11

| Ex No | Chemical name | Structure | Physical data MS (m/z) |
|---|---|---|---|
| 14 | (1R,2S,4R,5R,6R)-2-amino-4-{[5-(1-methylethyl)-4H-1,2,4-triazol-3-yl]sulfanyl}bicyclo[3.1.0]hexane-2,6-dicarboxylic acid | 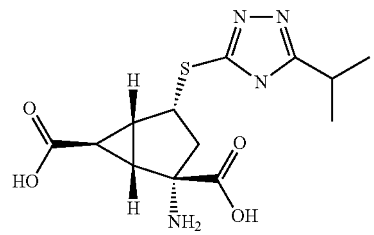 [SMILES: CC(C)c1nnc(S[C@@H]2C[C@@](N)(C(=O)O)[C@@H]3[C@@H](C(=O)O)[C@@H]32)[nH]1] | 327 (M + 1) |
| 15 | (1R,2S,4R,5R,6R)-2-amino-4-[(5-cyclopropyl-4H-1,2,4-triazol-3-yl)sulfanyl]bicyclo[3.1.0]hexane-2,6-dicarboxylic acid | 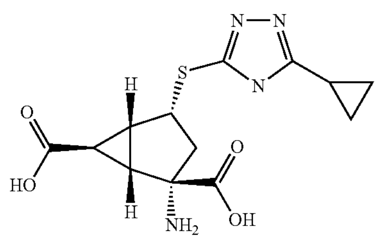 [SMILES: N[C@@]1(C(=O)O)C[C@@H](Sc2nnc(C3CC3)[nH]2)[C@H]2[C@H](C(=O)O)[C@H]21] | 325 (M + 1) |

Example 16

(1R,2S,4R,5R,6R)-2-[[(2S)-2-Aminopropanoyl]amino-4-[[5-(trifluoromethyl)-1H-1,2,4-triazol-3-yl]thio]bicyclo[3.1.0]hexane-2,6-dicarboxylic acid hydrochloride

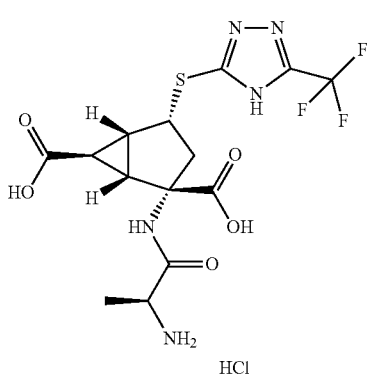 [SMILES: C[C@H](N)C(=O)N[C@@]1(C(=O)O)C[C@@H](Sc2nnc(C(F)(F)F)[nH]2)[C@H]2[C@H](C(=O)O)[C@H]21 ; Cl]

Treat (1R,2S,4R,5R,6R)-2-[2-((S)-tert-butoxycarbonylamino)-propionylamino]-4-(5-trifluoromethyl-1H-[1,2,4]triazol-3-ylsulfanyl)-bicyclo[3.1.0]hexane-2,6-dicarboxylic acid (340 mg, 0.65 mmol) with aqueous hydrochloric acid (2M, 7 mL) and stir at room temperature overnight. Concentrate the reaction mixture to dryness and purify the residue by cation-exchange chromatography (DOWEX® 50WX8-100). Dissolve the compound in water and adjust to pH=2. Allow the compound to flow through the column at a drip rate of about 1 drop every 1-2 seconds. After the initial loading volume has dropped to the resin surface, rinse with water (5 to 10 mL) and repeat 3 times. Monitor the pH of the effluent and continue rinsing with water until application complete (pH cycle observed: effluent from the column initially at pH=7 then drop to pH=1 and return back to pH=7). Wash the column with at least one column volume each of water, water:tetrahydrofuran (1:1) then water. Displace the product from the resin with 10% pyridine:water. Continue to elute with 10% pyridine:water until no additional product is eluted. Concentrate the fractions containing the product to obtain a colorless solid (204 mg). Dissolve the solid in water add 2M hydrochloric acid (1.5 eq) and freeze-dry the solution for 48 hours to give the title compound as a white solid (225 mg, 75.4%). MS (m/z): 424 (M+1).

The following compounds in Table 12 are prepared essentially following method of Example 16.

TABLE 12

| Ex No | Chemical name | Structure | Physical data MS (m/z) |
|---|---|---|---|
| 17 | (1R,2S,4R,5R,6R)-2-((S)-2-Amino-4-methylsulfanyl-butyrylamino)-4-(5-trifluoromethyl-1H-[1,2,4]triazol-3-ylsulfanyl)-bicyclo[3.1.0]hexane-2,6-dicarboxylic acid hydrochloride | 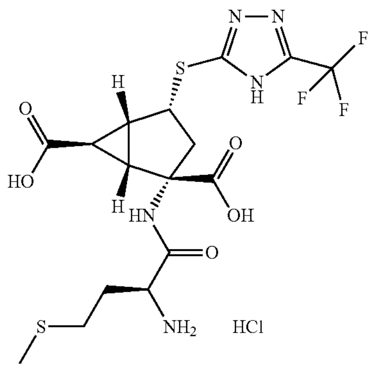 [SMILES: CSCC[C@H](N)C(=O)N[C@@]1(C(=O)O)C[C@@H](Sc2nnc(C(F)(F)F)[nH]2)[C@H]2[C@H](C(=O)O)[C@H]21 ; Cl] | 484 (M + 1) |
| 18 | (1R,2S,4R,5R,6R)-2-(glycylamino)-4-{[5-(trifluoromethyl)-1H-1,2,4-triazol-3-yl]sulfanyl}bicyclo[3.1.0]hexane-2,6-dicarboxylic acid hydrochloride | 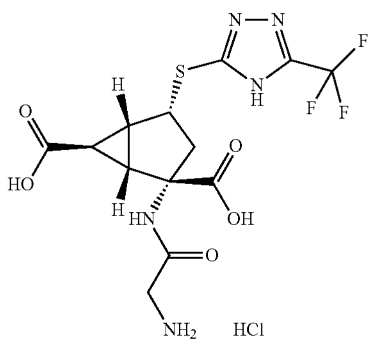 [SMILES: NCC(=O)N[C@@]1(C(=O)O)C[C@@H](Sc2nnc(C(F)(F)F)[nH]2)[C@H]2[C@H](C(=O)O)[C@H]21 ; Cl] | 411 (M + 1) |
| 19 | (1R,2S,4R,5R,6R)-2-[[(2S)-2-Aminopropanoyl]amino]4-(2H-1,2,3-triazol-4-ylsulfanyl)bicyclo[3.1.0]hexane-2,6-dicarboxylic acid hydrochloride | 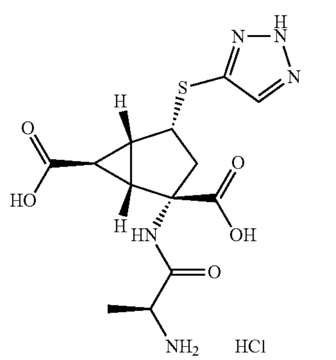 [SMILES: C[C@H](N)C(=O)N[C@@]1(C(=O)O)C[C@@H](Sc2cn[nH]n2)[C@H]2[C@H](C(=O)O)[C@H]21 ; Cl] | 356 (M + 1). |
| 20 | (1R,2S,4R,5R,6R)-2-(2-Amino-acetylamino)-4-(2H-[1,2,3]triazol-4-ylsulfanyl)-bicyclo[3.1.0]hexane-2,6-dicarboxylic acid hydrochloride | 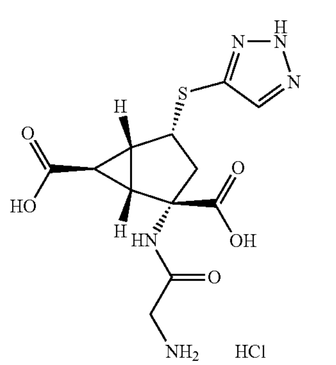 [SMILES: NCC(=O)N[C@@]1(C(=O)O)C[C@@H](Sc2cn[nH]n2)[C@H]2[C@H](C(=O)O)[C@H]21 ; Cl] | 342 (M + 1), 364 (M + 23) |

TABLE 12-continued

| Ex No | Chemical name | Structure | Physical data MS (m/z) |
|---|---|---|---|
| 21 | (1R,2S,4R,5R,6R)-2-((S)-2-Amino-4-methylsulfanyl-butyrylamino)-4-(2H-[1,2,3]triazol-4-ylsulfanyl)-bicyclo[3.1.0]hexane-2,6-dicarboxylic acid hydrochloride | 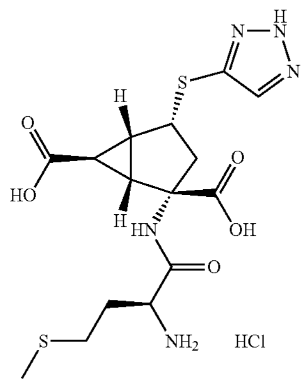 [SMILES: CSCC[C@H](N)C(=O)N[C@@]1(C(=O)O)C[C@@H](Sc2cn[nH]n2)[C@H]2[C@H](C(=O)O)[C@H]21 ; Cl] | 416 (M + 1), 438 (M + 23) |

Example 22

(1R,2S,4S,5R,6R)-2-[(-2-Aminoacetyl)amino]-4-(4H-1,2,4-triazol-3-ylsulfanyl)bicyclo[3.1.0]hexane-2,6-dicarboxylic acid hydrochloride

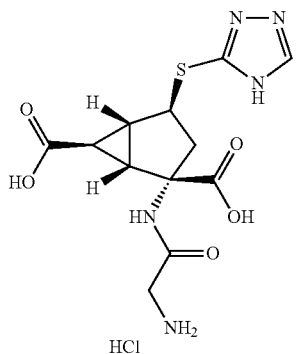 [SMILES: NCC(=O)N[C@@]1(C(=O)O)C[C@H](Sc2nnc[nH]2)[C@H]2[C@H](C(=O)O)[C@H]21 ; Cl]

Dissolve (1R,2S,4S,5R,6R)-2-[[-2-(tert-butoxycarbonylamino)acetyl]amino]-4-(4H-1,2,4-triazol-3-ylsulfanyl)bicyclo[3.1.0]hexane-2,6-dicarboxylic acid (220 mg, 0.49 mmol) in a saturated solution of hydrogen chloride gas in ethyl acetate (7 mL) and stir at room temperature for 2 hours. Remove the solvent to provide the title compound as a white solid (180 mg, 98%). MS (m/z): 342 (M+1).

The following compounds in Table 13 are prepared essentially following method of example 22.

TABLE 13

| Ex No | Chemical Name | Structure | Physical data MS (m/z) |
|---|---|---|---|
| 23 | (1R,2S,4S,5R,6R)-2-(L-alanylamino)-4-(4H-1,2,4-triazol-3-ylsulfanyl)bicyclo[3.1.0]hexane-2,6-dicarboxylic acid hydrochloride | 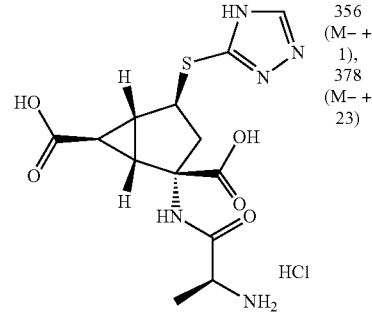 | 356 (M− + 1), 378 (M− + 23) |
| 24 | (1R,2S,4S,5R,6R)-2-(L-leucylamino)-4-(4H-1,2,4-triazol-3-ylsulfanyl)bicyclo[3.1.0]hexane-2,6-dicarboxylic acid hydrochloride | 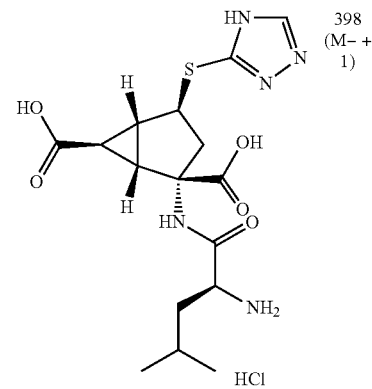 | 398 (M− + 1) |

TABLE 13-continued

| Ex No | Chemical Name | Structure | Physical data MS (m/z) |
|---|---|---|---|
| 25 | (1R,2S,4S,5R,6R)-2-(L-methionylamino)-4-(4H-1,2,4-triazol-3-ylsulfanyl)bicyclo[3.1.0]hexane-2,6-dicarboxylic acid hydrochloride | 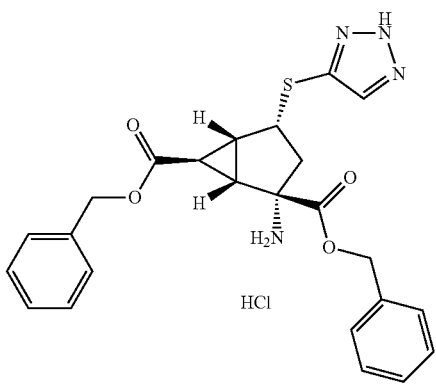 [SMILES: N[C@@]1(C(=O)OCc2ccccc2)C[C@@H](Sc2cn[nH]n2)[C@H]2[C@H](C(=O)OCc3ccccc3)[C@H]21 ; Cl] | 416 (M−+1) |

Example 26

Dibenzyl(1R,2S,4R,5R,6R)-2-amino-4-(1H-[1,2,3]triazol-4-ylsulfanyl)-bicyclo[3.1.0]hexane-2,6-dicarboxylate hydrochloride Add trifluoroacetic acid (3 mL, 40 mmol) to a solution of (1R,2S,4R,5R,6R)-2-tert-butoxycarbonylamino-4-(1H-[1,2,3]triazol-4-ylsulfanyl)-bicyclo[3.1.0]hexane-2,6-dicarboxylic acid dibenzyl ester (0.4 g, 0.71 mmol) in dichloromethane (12 mL) and stir at room temperature for 4.5 h. Concentrate the reaction mixture under reduced pressure, dissolve in acetonitrile (10 mL) and load onto a 10 g SCX-2 cartridge (preconditioned with acetonitrile). Wash the cartridge with acetonitrile (20 mL) then elute with a solution of 90:10 v/v acetonitrile/ammonium hydroxide (5×20 mL fractions). Evaporate fractions containing product and purify by silica gel chromatography (12 g silica column) eluting with 90:10:1 dichloromethane/methanol/ammonium hydroxide to obtain the product freebase as a colorless gum. Dissolve the gum in dichloromethane (10 mL), add hydrochloric acid (0.25 mL of a 2M solution in diethyl ether; 0.5 mmol), and evaporate solvent to obtain the title compound as a white solid (0.2 g, 56.3%). MS (m/z) 465 (M+1).

Example 27

Dibenzyl(1R,2S,4S,5R,6R)-2-amino-4-(1H-1,2,4-triazol-3ylsulfanyl)bicyclo[3.1.0]hexane-2,6-dicarboxylate

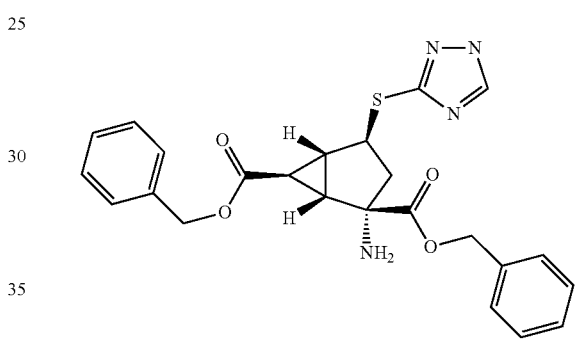

In a sealed tube, add p-toluensulfonic acid (5 eq) to a stirred solution of ditert-butyl(1R,2S,4S,5R,6R)-2-(tert-butoxycarbonylamino)-4-(1H-1,2,4-triazol-3-ylsulfanyl)bicyclo[3.1.0]hexane-2,6-dicarboxylate (1.00 g, 2.01 mmol) in benzyl alcohol (0.15 M). Heat the reaction mixture with stirring at 80° C. for 4 days. Cool the reaction mixture to room temperature. Pre-purify by SCX-2 column (10 g). Load the reaction mixture onto a column pre-conditioned with methanol, wash with methanol (×3) to remove the excess of the corresponding benzylic alcohol, and elute with 2N ammonia solution in methanol. Evaporate the solvent under reduced pressure to give a oil. The resulting oil is dissolved in ethyl acetate and washed with a saturated solution of sodium carbonate to remove the monoester formed in the reaction. The organic layer is dried and concentrated to give an oil. Purify the oil by flash chromatography eluting with dichloromethane/2N ammonium:methanol (98:2) to give the titled compound as a solid. (270 mg, 28%) MS (m/z): 465 (M+1)

The following compound in Table 14 is prepared essentially following method of Example 27.

TABLE 14

| Ex No | Chemical name | Structure | Phyiscal data MS (m/z) |
|---|---|---|---|
| 28 | Bis[[4-(trifluoromethyl)phenyl]methyl](1R,2S,4S,5R,6R)-2-amino-4-(1H-1,2,4-triazol-3-ylsulfanyl)bicyclo[3.1.0]hexane-2,6-dicarboxylate | 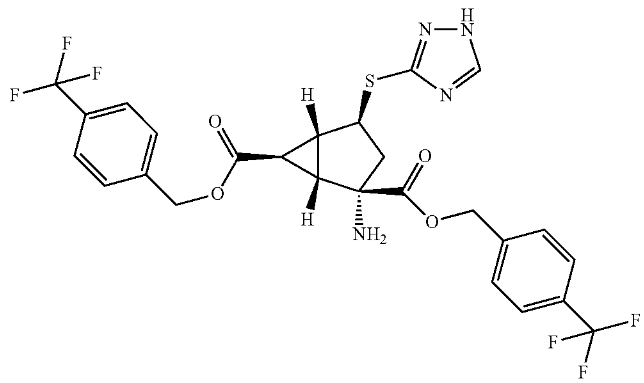 [SMILES: N[C@@]1(C(=O)OCc2ccc(C(F)(F)F)cc2)C[C@H](Sc2nc[nH]n2)[C@H]2[C@H](C(=O)OCc3ccc(C(F)(F)F)cc3)[C@H]21] | 601 (M + 1) |

Example 29

Bis[[2-(trifluoromethyl)phenyl]methyl](1R,2S,4S,5R,6R)-2-amino-4-(1H-1,2,4-triazol-3-ylsulfanyl)bicyclo[3.1.0]hexane-2,6-dicarboxylate hydrochloride

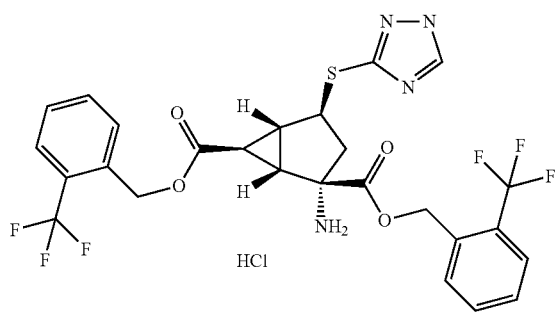 [SMILES: N[C@@]1(C(=O)OCc2ccccc2C(F)(F)F)C[C@H](Sc2nc[nH]n2)[C@H]2[C@H](C(=O)OCc3ccccc3C(F)(F)F)[C@H]21 ; Cl]

HCl

In a sealed tube, add p-toluensulfonic acid (3 eq) to a stirred solution of ditert-butyl(1R,2S,4S,5R,6R)-2-(tert-butoxycarbonylamino)-4-(1H-1,2,4-triazol-3-ylsulfanyl)bicyclo[3.1.0]hexane-2,6-dicarboxylate (500 mg, 1.01 mmol) in 2-trifluoromethylbenzylalcohol (30 eq). Heat the reaction mixture with stirring at 88° C. for 4 hours. Cool the reaction mixture to room temperature. Load the reaction mixture onto a SCX-2 column (10 g) pre-conditioned with methanol, wash with methanol (×3) to remove the excess of the corresponding benzylic alcohol then elute with 2N ammonia solution in methanol. Evaporate the solvent under reduced pressure to give an oil. The oil is treated with ethyl acetate resulting in a solid precipitate, which is the monoester. The solid is filtered and the filtrate is concentrated under reduced pressure to give an oil. Purify the oil by flash chromatography eluting with dichloromethane:methanol (95:5) to give the title compound as an oil (40 mg, 6%)

Dissolve bis[[2-(trifluoromethyl)phenyl]methyl](1R,2S,4S,5R,6R)-2-amino-4-(1H-1,2,4-triazol-3-ylsulfanyl)bicyclo[3.1.0]hexane-2,6-dicarboxylate (0.07 mmol), in a saturated solution of hydrogen chloride gas in ethyl acetate (1 mL). Stir the mixture (30 min) at room temperature. Remove solvent under reduced pressure and dry the resulting solid in a vacuum oven at 50° C. overnight. (30 mg, 65%) MS (m/z): 601 (M+1)

The following compounds in Table 15 are prepared essentially following method of example 29.

TABLE 15

| Ex No | Chemical name | Structure | Phyiscal data MS (m/z) |
|---|---|---|---|
| 30 | Bis[(2,4-difluorophenyl)methyl](1R,2S,4S,5R,6R)-2-amino-4-(1H-1,2,4-triazol-3-ylsulfanyl)bicyclo[3.1.0]hexane-2,6-dicarboxylate hydrochloride | 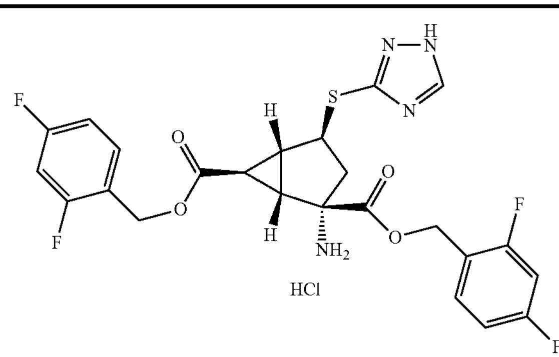 | 537 (M + 1) |

TABLE 15-continued

| Ex No | Chemical name | Structure | Phyiscal data MS (m/z) |
|---|---|---|---|
| 31 | Bis[(3-methoxyphenyl)methyl] (1R,2S,4S,5R,6R)-2-amino-4-(1H-1,2,4-triazol-3-ylsulfanyl)bicyclo[3.1.0]hexane-2,6-dicarboxylate hydrochloride | 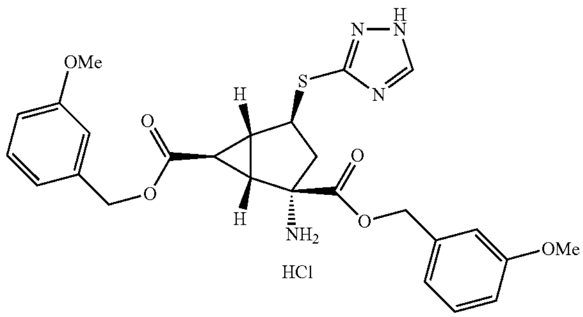 [SMILES: COc1cccc(COC(=O)[C@H]2[C@H]3[C@@H]2[C@](N)(C(=O)OCc2cccc(OC)c2)C[C@@H]3Sc2nc[nH]n2)c1 ; Cl] | 525 (M + 1) |
| 32 | Bis[(2-fluorophenyl)methyl] (1R,2S,4S,5R,6R)-2-amino-4-(1H-1,2,4-triazol-3-ylsulfanyl)bicyclo[3.1.0]hexane-2,6-dicarboxylate hydrochloride | 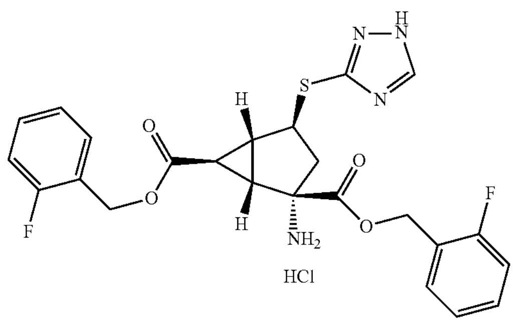 [SMILES: N[C@@]1(C(=O)OCc2ccccc2F)C[C@H](Sc2nc[nH]n2)[C@H]2[C@H](C(=O)OCc3ccccc3F)[C@H]21 ; Cl] | 501 (M + 1) |
| 33 | Bis[(3-fluorophenyl)methyl] (1R,2S,4S,5R,6R)-2-amino-4-(1H-1,2,4-triazol-3-ylsulfanyl)bicyclo[3.1.0]hexane-2,6-dicarboxylate hydrochloride | 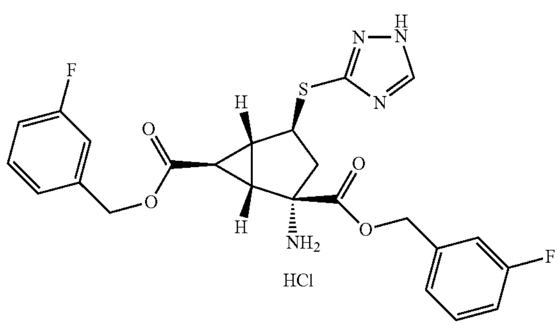 [SMILES: N[C@@]1(C(=O)OCc2cccc(F)c2)C[C@H](Sc2nc[nH]n2)[C@H]2[C@H](C(=O)OCc3cccc(F)c3)[C@H]21 ; Cl] | 501 (M + 1) |
| 34 | Bis[(4-fluorophenyl)methyl] (1R,2S,4S,5R,6R)-2-amino-4-(1H-1,2,4-triazol-3-ylsulfanyl)bicyclo[3.1.0]hexane-2,6-dicarboxylate hydrochloride | 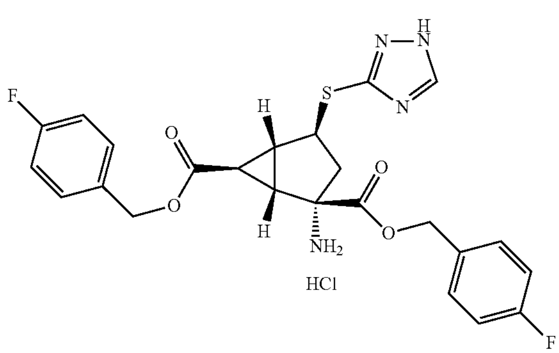 [SMILES: N[C@@]1(C(=O)OCc2ccc(F)cc2)C[C@H](Sc2nc[nH]n2)[C@H]2[C@H](C(=O)OCc3ccc(F)cc3)[C@H]21 ; Cl] | 501 (M + 1) |

Example 35

Bis[(4-methoxybenzyl)(1R,2S,4S,5R,6R)-2-amino-4-(1H-[1,2,4]triazol-3-ylsulfanyl)bicyclo[3.1.0]hexane-2,6-dicarboxylate

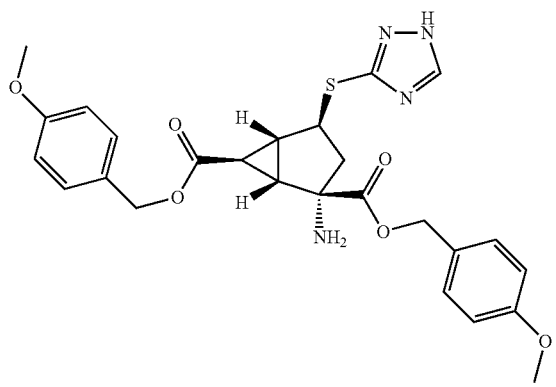 [SMILES: COc1ccc(COC(=O)[C@H]2[C@H]3[C@@H]2[C@](N)(C(=O)OCc2ccc(OC)cc2)C[C@@H]3Sc2nc[nH]n2)cc1]

Dissolve bis-(4-methoxy-benzyl)(1R,2S,4S,5R,6R)-2-tert-butoxycarbonylamino-4-(1H-[1,2,4]triazol-3-ylsulfanyl)-bicyclo[3.1.0]hexane-2,6-dicarboxylate (102 mg, 163.3 μmol) in a saturated solution of hydrogen chloride gas in ethyl acetate (0.5 mL) and stir at room temperature for 10 min. Remove the solvent. Load the reaction mixture onto an SCX column pre-conditioned with acetonitrile, wash with acetonitrile (×2) then elute with 2N ammonia solution in methanol: acetonitrile (2 column volumes then evaporate the solvent under reduced pressure. Purify the crude residue via silica gel chromatography (4 g), eluting with a gradient of dichloromethane/6% 2N ammonia solution in methanol to provide the title compound (30 mg, 37%). MS (m/z): 525 (M+1).

Example 36

Bis[3-(trifluoromethyl)benzyl](1R,2S,4S,5R,6R)-2-amino-4-(1H-1,2,4-triazol-3-ylsulfanyl)bicyclo[3.1.0]hexane-2,6-dicarboxylate hydrochloride

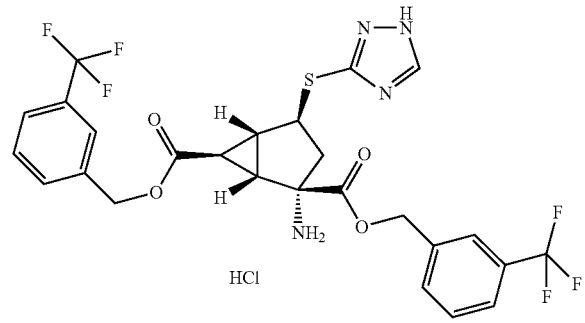 [SMILES: N[C@@]1(C(=O)OCc2cccc(C(F)(F)F)c2)C[C@H](Sc2nc[nH]n2)[C@H]2[C@H](C(=O)OCc3cccc(C(F)(F)F)c3)[C@H]21 ; Cl]

(1R,2S,4S,5R,6R)-2-tert-Butoxycarbonylamino-4-(1H-[1,2,4]triazol-3-ylsulfanyl)-bicyclo[3.1.0]hexane-2,6-dicarboxylic acid bis-(3-trifluoromethyl-benzyl) ester (200 mg, 285 μmol) is dissolved in a saturated solution of hydrogen chloride gas in ethyl acetate (2 mL) and stir at room temperature. After 2 h, conversion to the desired product is total. Therefore solvent is removed in vaquo. Solid washed with Ethyl Acetate and dried at 50° C. in vaquo overnight to give title, 0.17 g (94%), %). MS (m/z): 601 (M+1).

Example 37

Bis-(2,2-Dimethyl-propionyloxymethyl)(1R,2S,4S,5R,6R)-2-amino-4-(1H-[1,2,4]triazol-3-ylsulfanyl)-bicyclo[3.1.0]hexane-2,6-dicarboxylate

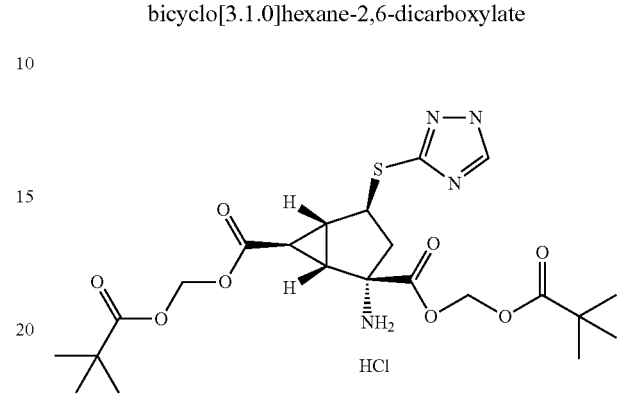

Dissolve bis(2,2-dimethylpropanoyloxymethyl)(1R,2S,4S,5R,6R)-2-(tert-butoxycarbonylamino)-4-(1H-1,2,4-triazol-3-ylsulfanyl)bicyclo[3.1.0]hexane-2,6-dicarboxylate (98 mg, 156 μmol) in a saturated solution of hydrogen chloride gas in ethyl acetate (2 mL) and stir at room temperature for 2 hours. Remove the solvent. A white solid obtained for desired compound (68 mg, 79%). MS (m/z): 399 (M+1).

Example 38

4-Benzyl-6-ethyl(1R,2S,4S,5R,6R)-2-amino-4-(1H-1,2,4-triazol-3-ylsulfanyl)bicyclo[3.1.0]hexane-2,6-dicarboxylate hydrochloride

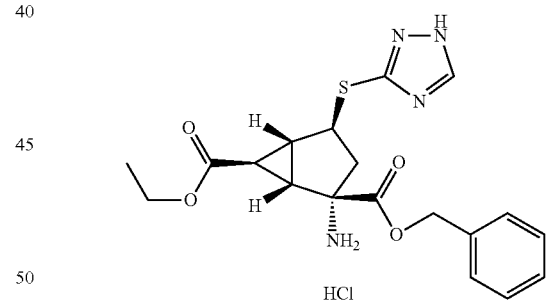

Dissolve 2-benzyl-6-ethyl(1R,2S,4S,5R,6R)-2-tert-butoxycarbonylamino-4-(1H-[1,2,4]triazol-3-ylsulfanyl)-bicyclo[3.1.0]hexane-2,6-dicarboxylate (78 mg, 155.20 μmol) in a saturated solution of hydrogen chloride gas in ethyl acetate (2 mL) and stir at room temperature for 2 hours. Remove the solvent. The title compound is obtained as a white solid (60 mg, 91%). MS (m/z): 403 (M+1).

The mGlu receptors are G-protein-coupled receptors that modulate neuronal excitability. Although dysregulated glutamate neurotransmission has been linked to schizophrenia, all commonly prescribed antipsychotics act on dopamine receptors. Various studies support Group II mGlu receptor (which includes mGlu2, mGlu3, or both) activation for the treatment of schizophrenia. In particular, recent data demonstrate that a mGlu 2/3 receptor agonist has antipsychotic properties and may provide a new alternative for the treatment of schizophrenia (Patil et al., *Nature Medicine* (2007) 13(3), 1102-1107). Preclinical studies using gene deletion mice suggest that the antipsychotic-like activity of mGlu2/3 agonists are predominantly mGlu2 receptor mediated. Additional preclinical efficacy models indicate anxiolytic, antidepressant, and neuroprotective properties of mGlu2/3 receptor agonists. Therefore, mGlu2 agonists may be useful in the treatment of psychiatric disorders, such as bipolar disorder, schizophrenia, depression, and generalized anxiety disorder.

Human mGlu2 Agonist FLIPR® Assay

AV-12 cell lines, derived from Syrian Hamster fibroblasts and stably expressing the human mGlu2 receptor and co-transfected with the rat glutamate transporter EAAT 1 (Excitatory Amino Acid Transporter 1) and the Gα15 subunit, are used for these studies. The expression of Gα15 allows Gi-coupled receptors to signal through the phospholipase C pathway, resulting in the ability to measure receptor activation by a fluorometric calcium response assay. The cell lines are maintained by culturing in Dulbecco's Modified Eagle's Medium (DMEM) with high glucose and pyridoxine hydrochloride supplemented with 5% dialyzed fetal bovine serum, 1 mM sodium pyruvate, 10 mM HEPES [4-(2-hydroxyethyl)-1-piperazineethanesulfonic acid], 1 mM of L-glutamine, and 5 μg/mL blasticidin (all media are purchased from Invitrogen). Confluent cultures are passaged biweekly using an enzyme-free dissociation solution (Chemicon S-004-B). Cells are harvested 24 hours prior to assay and dispensed using a Matrix Well-Mate cell seeder at 85,000 (mGlu2) or 115,000 (mGlu3) cells per well into 96-well, black-walled, poly-D-lysine-coated plates (BD BioCoat #354640) in medium containing only 250 (mGlu2) or 125 (mGlu3) μM L-glutamine (freshly added).

Intracellular calcium levels are monitored before and after the addition of compounds using a Fluorometric Imaging Plate Reader (FLIPR®, Molecular Devices). The assay buffer is comprised of Hank's Buffered Salt Solution (HBSS; Sigma) supplemented with 20 mM HEPES. The medium is removed and the cells are incubated with 8 μM Fluo-3AM (Molecular Probes, F-1241; 50 μL per well) in assay buffer for 90 minutes at 25° C. The dye solution is removed and replaced with fresh assay buffer (50 μL per well). A single-addition FLIPR® assay generating an 11-point concentration response curve (3× dilutions starting at 10 μM) for the agonist glutamate (Fisher A125-100) is conducted prior to each experiment to confirm the typical $EC_{50}$ response. Results are analyzed using PRISM® v4.03 (GraphPad Software). Exemplified compounds of the present invention are tested in a single-addition FLIPR® assay using a 10-point concentration response profile using 3× dilutions starting at a final concentration of 25 μM. Exemplified compounds of the present invention are solubilized as 10 mM stocks in 0.1N NaOH and stored at –20 C. They are diluted through a three-fold dilution series into assay buffer. After taking an initial 5-sec fluorescent read on the FLIPR® instrument, a compound of the present invention is added to the cell plate (50 μL per well). Data are collected every second for the first 30 seconds and then every 3 seconds for a total of 90 seconds in order to detect agonist activity. The maximal response is defined as that induced by ECmax (100 μM glutamate). The compound effect is measured as maximal minus minimal peak heights in relative fluorescent units (RFUs) corrected for basal fluorescence measured in the absence of glutamate. Determinations are carried out using single plates. Agonist effects are quantified as percent stimulation induced by compound alone relative to the maximal glutamate response. All data are calculated as relative $EC_{50}$ values using a four-parameter logistic curve fitting program (ACTIVITY BASE® v5.3.1.22).

The compounds exemplified herein were tested essentially as described above and exhibited a relative $EC_{50}$ value in the hMGLUR2 FLIPR® Assay of lower than 0.5 μM.

The following exemplified compounds in Table 16 were tested essentially as described above and exhibited the following activity:

TABLE 16

| hMGLUR2 FLIPR ® Assay Summary | | |
|---|---|---|
| Ex No | Relative $EC_{50}$ (nM) | Relative % Efficacy |
| 1 | 46 | 92.6 |
| 2 | 57.2 | 78.5 |
| 10 | 69.1 | 89.0 |
| 12 | 5.18 | 92.1 |

These data summarize the activity of the compounds of Table 16 for functional agonist activity in the hmGlu2 FLIPR® assay and demonstrate that the compounds are mGlu2 agonists.

Reversal of Phencyclidine (PCP)-Induced Hyperlocomotor Activity in Rats

Administration of NMDA receptor antagonists, such as ketamine or phencyclidine (PCP), produces psychotomimetic-like effects in humans that are similar to those symptoms observed in patients with schizophrenia. The ability of agents to reverse the locomotor-stimulating effects of NMDA antagonists are often used as an animal model of psychosis, demonstrating good predictive validity for detecting clinical efficacy of medications for schizophrenia and bipolar disorder.

Motor activity is monitored by placing individual male, Sprague-Dawley (Harlan, Indianapolis, Ind.) rats in transparent, plastic shoe-box cages of the dimensions 45×25×20 cm, with 1 cm depth of wood chips as bedding, and a metal grill on top of the cage. Motor monitors (Kinder Scientific) consist of a rectangular rack of 12 photobeams arranged in an 8×4 formation, (or a high density grouping of 22 in a 15×7 pattern) at a height of 5 cm, with a second rack (for measuring rearing behaviors) at a height of 15 cm. The shoe box cage is placed inside of these racks, with the racks on a 3 foot high tabletop in an isolated room. A compound of the present invention is dosed (intraperitoneal route (i.p.), non-prodrug) within a range of 0.3-10 mg/kg, 30 minutes prior to a 5 mg/kg challenge dose of phencyclidine (PCP). A compound of the present invention is dosed (oral route, prodrug) within a range of 0.3-30 mg/kg, in overnight fasted rats, 4 hours prior to a 5 mg/kg challenge dose of PCP. On the test day, rats are placed in the test cage and allowed to acclimate for 30 minutes prior to PCP challenge; rats are monitored for an additional 60 minutes following PCP administration.

Data analysis and $ED_{50}$ calculations are conducted using GraphPad PRISM® (San Diego, Calif. USA). Power analyses have determined that 8-10 rats per group are needed to have appropriate statistical power for detecting treatment differences (power=0.8). A one-way analysis of variance (ANOVA) with a post-hoc Dunnett's multiple comparison test is conducted on the total 60 minute locomotor activity. $ED_{50}$ calculations are performed using non-linear regression curve fitting on percent reversal transformed data for each dose.

The compound of Example 10 and its corresponding prodrug (Example 25) were measured in this assay, run substantially as above, resulted in $ED_{50}$ values of 0.9 mg/kg (i.p. administration) and 6.4 mg/kg (oral administration), respectively. These results demonstrate that the active parent and its prodrug form exhibit robust efficacy in this pharmacological model predictive of efficacy in patients suffering from schizophrenia and bipolar disorder.

Reversal of Phencyclidine (PCP)-Induced Hyperlocomotor Activity in Mice

This assay for Reversal of Phencyclidine (PCP)-Induced Hyperlocomotor Activity in Mice is run substantially as the Reversal of Phencyclidine (PCP)-Induced Hyperlocomotor Activity in Rats assay provided above, using mice instead of rats and with the changes noted below.

Motor activity is monitored by placing individual male, ICR (CD-1), (Harlan, Indianapolis, Ind.) mice in transparent, plastic shoe-box cages of the dimensions 45×25×20 cm, with 0.5 cm depth of wood chips as bedding, and plastic lid on top of the cage. Motor monitors (Kinder Scientific) consist of a rectangular rack of 12 photobeams arranged in an 8×4 formation, (or a high density grouping of 22 in a 15×7 pattern) at a height of 2.5 cm. The shoe box cage is placed inside of these racks, with the racks on a 3 foot high tabletop in an isolated room. A compound of the present invention is dosed (intraperitoneal route, non-prodrug) usually within a range of 0.3-30 mg/kg; though higher doses may be used, 30 minutes prior to a 7.5 mg/kg challenge dose of phencyclidine (PCP). On the test day, mice are placed in the test cage and allowed to acclimate for 45 minutes prior to PCP challenge; mice are monitored for an additional 60 minutes following PCP administration.

Power analyses have determined that 7-8 mice per group are needed to have appropriate statistical power for detecting treatment differences (power=0.8).

Dose response experiments were conducted on Examples 1, 2, 3, and 11 following i.p. administration. The $ED_{50}$ values were as follows: Example 1=18.4 mg/kg; Example 2=14.4 and 14.3 (2 independent experiments); Example 3=17.1 mg/kg; Example 11=1.2 mg/kg. Finally, Example 8 reversed PCP-induced locomotor activity by 52% following a single dose of 10 mg/kg. These results demonstrate that exemplified compounds within the scope of the present invention are useful medications for schizophrenia and bipolar disorder.

Attenuation of Stress-Induced Hyperthermia in Rats

Hyperthermia, a rise in core body temperature, is a general phenomenon that has been reliably demonstrated in many mammals, including humans, in response to stress. In many anxiety disorders, hyperthermia occurs as part of the pathology and is considered a symptom of the disease. Compounds which attenuate stress-induced hyperthermia in animals are believed to be useful in treating anxiety disorders in humans. Generalized anxiety disorder is an example of such disorders that may be treated with such compounds. The conventional and minimally-invasive method for analyzing stress-induced hyperthermia is by measuring body temperature, and stress-induced increases in body temperature, via rectal thermometer. Male Fischer F-344 rats (Harlan, Indianapolis, Ind., USA) weighing between 275-350 g are tested. All animals are individually-housed with food and automated water available ad libitum, and maintained on a 12 h light/dark cycle (lights on at 06:00) Animals are fasted for approximately 12-18 hours before the experiment, which is conducted during the light phase. Rats are dosed one hour prior to the experiment by intraperitoneal (i.p.) route of administration in a dose volume of 1 mL/kg. The vehicle used was water with enough NaOH added to achieve a pH between 5-7. The mGluR5 antagonist MTEP (3-[(2-methyl-1,3-thiazol-4-yl)ethynyl] pyridine) and mGlu2/3 agonist LY317206 were used as quality controls, given that they produced reliable efficacy in this model Immediately following dosing, rats are returned to their home cage, and the experimenter turns off the lights and leaves the room. The dosing room is darkened for the remainder of the 1-hr pretreatment period.

After the pretreatment period, rats are taken individually to a brightly lit adjacent room where baseline body temperatures are determined by insertion of a rectal probe lubricated with mineral oil. Body temperature is assessed using a PHYSITEMP BAT-12® Microprobe Thermometer with a PHYSITEMP RET-2® rat rectal probe (Physitemp Instruments Inc., Clifton, N.J., USA). The probe is inserted approximately 2 cm into the rectum, to measure the core body temperature (this is the baseline body temperature, T1, in degrees Celsius). Ten minutes later a second body temperature measurement is recorded (T2). The difference in body temperature (T2−T1) is defined as the stress-induced hyperthermic response. The dose at which a compound of the present invention produces a 35% reduction in stress-induced hyperthermic response, relative to the vehicle response, is defined as the $T_{35}$ dose.

The compound of Example 10 was measured in this assay run substantially as above to have a $T_{35}$ of 1.7 mg/kg and a maximal reduction of stress-induced hyperthermia of 75% at 10 mg/kg. In comparison, MTEP (3 mg/kg) and LY317206 (20 mg/kg) reduced stress-induced hyperthermia by 53% and 32%, respectively. These results demonstrate that mGlu2 agonist activity produces an anxiolytic-like effect in this rat model of stress-induced anxiety and are consistent with reported anxiolytic activity of mGlu2/3 agonists in preclinical (Imre (2007) CNS Drug Rev. 13: 444-464) and clinical (Dunayevich et al., (2008) Neuropsychopharm. 33: 1603-1610) studies. These results suggest potential clinical utility of mGlu2 agonism for the treatment of anxiety disorders.

Forced Swim Test in Rodents

The rodent forced swim test assay is well characterized and displays good predictive validity for detecting antidepressant-like activity of current medications for major depressive disorder. In this assay, mechanisms with purported antidepressant-like activity decrease immobility in a brief inescapable forced swim episode.

The forced-swim test was conducted in mice (male, NIH-Swiss mice, 20-25 g, Harlan Sprague-Dawley, Indianapolis, Ind.). Mice are placed in clear plastic cylinders (diameter 10 cm; height: 25 cm) filled to 6 cm with 22-25° C. water for six min. The duration of immobility is recorded during the last 4 min of a six-minute trial. The compounds of Examples 2, 3, 8, 11, and 12 are tested following intraperitoneal dosing, 60 min prior to testing. Imipramine is used as a positive control for these studies. Compounds are formulated in a water vehicle, with minimal NaOH added. The amount of time spent immobile (defined as movements only necessary to keep the subject's head above water) is the dependent measure and recorded by an observer blinded to the drug treatment of the subjects. Data are analyzed by post-hoc Dunnett's test with alpha level set at 0.05. An $ED_{60}$ value (60% of the amount of immobility relative to vehicle controls) is calculated to estimate potency of the test compounds.

Example 2 was tested in two independent experiments and produced $ED_{60}$ values of 9.8 and 4.2 mg/kg. Example 3 was more potent and the $ED_{60}$ value was estimated to be less than the lowest dose tested of 3 mg/kg. The $ED_{60}$ for Example 8 was 7.95 mg/kg. Example 11 had an $ED_{60}$ of 0.88 mg/kg; however, efficacy was lost in a second study in which higher doses (3-30 mg/kg) were evaluated. Example 12 produced and $ED_{60}$ of 3.31 mg/kg. These results demonstrate that compounds within the scope of the present invention are potentially useful medications for depression.

In Vitro PepT1 GlySar Inhibition Screen and $IC_{50}$ Determination

PepT1 assays are established to examine the ability of the amino acid prodrug compounds to interact with the intestinal absorption transporter PepT1.

HeLa cells, derived from human cancer cells, (American Type Culture Collection) are grown in Hyclone Medium (Invitrogen, Cat# SH30243) containing 10% fetal bovine serum (FBS), 0.1 mM non essential amino acids (NEAA), and 100 units/mL penicillin with 100 µg/mL streptomycin at 37° C. in a 5% $CO_2$ humidified atmosphere. The cell line is used for up to 40 passages and then discarded. Frozen cells in 1 mL vials are thawed in water bath for 1-2 minutes and added to 5 mL of cell medium at 37° C. Each of the T-flasks is provided with 8.5 mL of the fresh medium and 1.5 mL of the cell stock. Cells are passaged twice during a week. This is achieved by rinsing the flasks with 10 mL of phosphate buffered saline-ethylene diaminetetra acetic acid (PBS-EDTA), adding 2 mL of trypsin for 2-5 minutes, to detach the cells, and adding 8 mL of fresh medium to inhibit further activity of trypsin. Each new flask receives a combination of 8.5 mL of fresh medium and 1.5 mL of cell stock, in order to obtain 1:6 cell dilution. Cells are incubated at 37° C., until ready for the uptake study.

Cells that are 70-80% confluent in the T-flasks are plated 1 day prior to the transfection procedure. The flask with the cell stock is treated with PBS-EDTA and trypsin to detach the cells, and transfection medium is used from this point. Transfection medium consists of Dulbecco's Modified Eagle Medium (DMEM)+NEAA. To each well, 0.5 mL of the cell mixture is added ($1.3\times10^5$ is the desired cell concentration) and the cells are incubated at 37° C. overnight. Twenty four hours before the assay, cells are transfected with PEPT1. Transfection mixture is prepared by mixing 600 µL of serum free transfection medium, 18 µL of FUGENE6® (Roche Diagnostics), and 11 µg of the PepT1 DNA. The transfection reagent-DNA complex is incubated for 20 minutes and 24 µL of the reagent-DNA complex is added to each well.

Inhibition of PEPT1-mediated [glycyl-1-2-$^{14}$C]Glyclysarcosine (GlySar) uptake activity is measured in the cells cultured in the 24-well plates 24-hours post transfection as previously published (Zhang et al. 2004. J. Pharm. Exper Ther. 310:437-445). To measure the ability of a compound of the present invention to inhibit the uptake of [$^{14}$C]Gly-Sar, prodrug compounds are incubated with 80 to 90% confluent PepT1 transiently transfected HeLa cells at 5 mM in pH 6.0 uptake medium in the presence of 5 µM [$^{14}$C]Gly-Sar (Moravek Biochemicals) and 20 µM cold Gly-Sar. Uptake media consists of 140 mM NaCl, 5.4 mM KCl, 1.8 mM $CaCl_2$, 0.8 mM $MgSO_4$, 5 mM Glucose, 25 mM tris(hydroxymethyl)aminomethane buffer (TRIS). The solution is then brought to pH 6.0 using 2-(N-morpholino)ethanesulfonic acid. The incubation volume is 500 µL and is performed at room temperature for 3 minutes. To stop the uptake at the conclusion of the incubation time, the uptake media is aspirated off of the cell monolayer and 500 µL of ice cold PBS added to the well. The cells are washed 3 times with 500 µL of room temperature PBS without $Ca^{+2}$ and $Mg^{+2}$. The cells are then lysed with 300 µL of 1% TRITON® X100 $H_2O$ solution. A 200 µL aliquot is removed and radioactivity is determined by liquid scintillation counting to measure the [$^{14}$C]Gly-Sar present in each of the incubation wells. A no inhibitor control is established and the percent inhibition of each prodrug is calculated with respect to this control. A negative control (Glycine) and two positive controls (cefadroxil and cefalexin) are performed in parallel with each experiment to demonstrate viability of the assay system. Prodrug compounds with GlySar uptake inhibition equal or better than cephalexin are considered acceptable. Mean values±standard deviation are 10.1±9.5% (n=19) for Glycine, 53.2±13.2% (n=19) for Cefadroxil, and 37.5±14.7% (n=18) for Cephalexin.

For the PepT $IC_{50}$ assay, prodrug compounds are incubated at a range of concentrations (0.0625 to 25 mM) in the presence of 5 µm [$^{14}$C]Gly-Sar and 20 µM cold Gly-Sar. The incubation and sampling procedures are exactly the same as the PepT1 screen described above. [$^{14}$C]Gly-Sar uptake data are evaluated for each of the prodrug compound concentrations and $IC_{50}$ values are calculated.

The following compounds were tested essentially as described above and exhibited the following activity:

TABLE 17

| Example | Mean GlySar Uptake Inhibition % |
|---|---|
| 16 | 53.9% |
| 21 | 57.4% |
| 22 | 46.7% |
| 24 | 47.1% |

These results demonstrate that the compounds of Table 17 are capable of being orally absorbed via the PepT1 transporter and are as good as or better than cefadroxil and cephalexin (Zhang et al, 2004. JPET 310:437-445), which is predictive of human oral absorption via the PepT1 transporter.

In Vitro Intestinal Prodrug Hydrolysis Assay

Frozen human duodenum intestinal homogenates (1:2 tissue:buffer ratio using 100 mM Tris Phosphate buffer, pH 7.4) are obtained from Celsius In Vitro Technologies (Baltimore, Md.) that were both phenylmethylsulphonylfluoride (PMSF) and EDTA free.

Each lot of human duodenum is obtained from a single donor and the intestine is scraped and the sections are frozen separate. All original tissue collections are performed at 4° C. and immediately frozen at −70° C. Human intestinal homogenates are thawed and diluted to a final protein concentration of 0.5 mg/mL in 100 mM PBS buffer, pH 7.4 immediately prior to the incubations.

Incubations are conducted in 96-well plates and all prodrug compounds are run in duplicate on each day. Stock prodrug compound solutions are prepared in water at a concentration of 1 mM. A 200 µL aliquot of 0.5 mg/mL intestinal homogenate and 196 µL of 100 mM PBS buffer are placed in a 96-well plate in a 37° C. water bath. To ensure hydrolysis is not due to chemical instability, prodrug compounds are also incubated with PBS buffer alone without intestinal homogenate. Using a 96-well pipettor, 4 µL of the 1 mM prodrug compound solution is transferred into the homogenate Immediately after addition of the prodrug compound (time zero) and after 1 hour incubation, 50 µL samples of the incubation mixture are removed using an automated disposable simultaneous 96 well pipettor and added directly to 200 µL of methanol quench solution containing 100 ng/mL of Internal Standard. The samples are then centrifuged at 3500 rpm for 5 minutes at 10° C. The supernatant (200 µL) is transferred to a final 96 well PCR plate and sealed for analysis by LC/MS/MS.

Concentrations of hydrolyzed compounds of the present invention in the incubation mixtures are determined using LC/MS/MS detection on a Sciex API 4000™ quadrapole mass spectrometer with Analyst version 1.4.2, TURBOIONSPRAY®, positive ionization, and Selected Reaction Monitoring (SRM). A Waters ATLANTIS® T3 (20×2.1 mm, 5 µM) HPLC column is used at ambient temperature with a flow rate of 1.0 mL/min and a mobile phase gradient from 0.1% mobile phase A to 99% mobile phase A. Mobile phase A is 1000:5 water:heptafluorobuteric acid and mobile phase B is 1:1 methanol:glacial acetic acid.

Concentrations of hydrolyzed compounds of the present invention in the intestinal incubation mixtures are determined from standard curves prepared by replicate two-fold dilution starting at 10 µM in 100 mM PBS pH 7.4 and subsequently quenched with methanol-internal standard solution identical to the samples. Averages and standard deviations are calculated using MICROSOFT® Office EXCEL® 2007. Amount of hydrolysis is determined as a molar percentage of compound formed relative to prodrug compound concentration added. Hydrolysis of the positive control, Internal Prodrug Compound A to Internal Compound Drug A, run in every batch averaged 75.3% (n=20). Final values are then normalized relative to the formation of Internal Compound Drug A.

The following compounds were tested essentially as described above and exhibited the following activity:

TABLE 18

| Ex No | In Vitro Human Intestinal Hydrolysis % (relative to positive control) |
|---|---|
| 17 | 63.3% |
| 18 | 65.5% |
| 19 | 58.1% |
| 21 | 63.8% |

These results demonstrate that the compounds of Table 18 are capable of being hydrolyzed in the human intestine.

In Vitro Human Liver S-9 Homogenate Hydrolysis Assay

Liver S9 fractions are obtained from Xenotech LLC (Lenexa, Mo.). The lot is from a pool of two donors, one male and one female. The liver S9 fraction is prepared and diluted using a homogenization buffer consisting of 50 mM Tris, pH 7.4 at 4° C. and 150 mM potassium chloride without EDTA. Prodrug compounds are incubated in the liver homogenate for 2 hours at 37° C., after which the concentration of compound is determined by LC/MS/MS. Hydrolysis of Clopidogrel to Clopidogrel Carboxylic Acid is utilized as an assay positive control.

Incubations are conducted in 96-well format and all prodrug compounds are run in duplicate on each day. Stock prodrug compound solutions are prepared in water at a concentration of 1 mM. Human liver S9 fraction is diluted to a final protein concentration of 0.5 mg/mL in 100 mM PBS buffer, pH 7.4.

A 200 µL aliquot of 0.5 mg/mL human liver S-9 homogenate and 196 µL of 100 mM PBS buffer are placed in a 96-well plate in a 37° C. water bath. Using a 96-well pipettor, 4 µL of the 1 mM prodrug solution is transferred into the homogenate. To ensure hydrolysis is not due to chemical instability, prodrug compounds are also incubated with PBS buffer alone without liver S-9 Immediately after addition of the prodrug compound (time zero) and after 1 hour incubation, 50 µL samples of the incubation mixture are removed using an automated disposable simultaneous 96-well pipettor and added directly to 200 µL of methanol quench solution containing 100 ng/mL of Internal Standard. The samples are then centrifuged at 3500 rpm for 5 minutes at 10° C. The supernatant (200 uL) is transferred to a final 96 well PCR plate and sealed for analysis by LC/MS/MS.

LC/MS/MS quantification of compound formed during the incubation is performed on a Sciex API 4000, Analyst version 1.4.2, TURBOIONSPRAY®, positive ionization, and Selected Reaction Monitoring (SRM). The HPLC column used is a Waters ATLANTIS® T3 (20×2.1 mm, 5 µm) at ambient temperature with a mobile phase flow rate of 1.0 mL/min. Mobile phase A is 1000:5 water:heptafluorobuteric acid and mobile phase B is 1:1 methanol/glacial acetic acid. A mobile phase gradient is utilized starting mobile phase ratio A/B of 99.9/0.1 and finishing at 1/99.

Concentrations of hydrolyzed compound in the incubation mixtures are determined from standard curves prepared by replicate two-fold dilution starting at 10 µM in 100 mM PBS pH 7.4 and subsequently quenched with methanol-internal standard solution identical to the samples. Averages and standard deviations are calculated using MICROSOFT® Office EXCEL® 2007. Final values are presented as a molar percentage of compound formed relative to prodrug compound concentration added. Hydrolysis of Clopidogrel to Clopidogrel Carboxylic Acid is used as the positive control and averages 73.0% (n=27).

The following compounds were tested essentially as described above and exhibited the following activity:

TABLE 19

| Ex No | In Vitro Human Liver S9 Hydrolysis % |
|---|---|
| 26 | 41.2% |
| 30 | 15.9% |
| 32 | 19.6% |
| 37 | 32.7% |

These results demonstrate that the compounds of Table 19 are capable of being hydrolyzed in the human liver.

The compounds of the present invention are preferably formulated as pharmaceutical compositions using one or more pharmaceutically acceptable carriers, diluents, or excipients and administered by a variety of routes. Preferably, such compositions are for oral or intravenous administration. Such pharmaceutical compositions and processes for preparing them are well known in the art. See, e.g., Remington: The Science and Practice of Pharmacy (A. Gennaro, et al., eds., 21st ed., Mack Publishing Co., 2005).

The compounds of the present invention are generally effective over a wide dosage range. For example, dosages per day normally fall within the range of about 0.3 to about 30 mg/kg of body weight. In some instances dosage levels below the lower limit of the aforesaid range may be more than adequate, while in other cases still larger doses may be employed, and therefore the above dosage range is not intended to limit the scope of the invention in any way. It will be understood that the amount of the compound actually administered will be determined by a physician, in the light of the relevant circumstances, including the condition to be treated, the chosen route of administration, the actual compound or compounds administered, the age, weight, and response of the individual patient, and the severity of the patient's symptoms.

We claim:
1. A compound of the formula

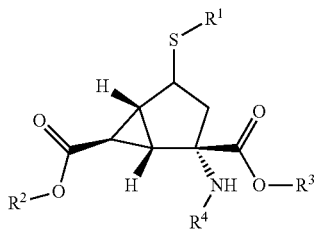

wherein
$R^1$ is

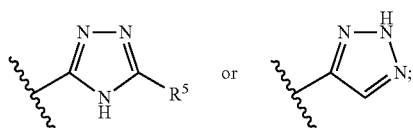

$R^2$ is hydrogen, 2,2-dimethyl-propionyloxymethyl, or benzyl, wherein benzyl is optionally substituted with one to two fluorine atoms, —$C_1$-$C_3$ alkyl optionally substituted with 1 to 3 fluorine atoms, or —$C_1$-$C_3$ alkoxy;

$R^3$ is hydrogen, 2,2-dimethyl-propionyloxymethyl, or benzyl, wherein benzyl is optionally substituted with one to two fluorine atoms, —$C_1$-$C_3$ alkyl optionally substituted with 1 to 3 fluorine atoms, or —$C_1$-$C_3$ alkoxy;

$R^4$ is hydrogen, (2S)-2-aminopropanoyl, (2S)-2-amino-4-methylsulfanyl-butanoyl, (2S)-2-amino-4-methyl-pentanoyl, or 2-aminoacetyl; and $R^5$ is —$C_1$-$C_3$ alkyl optionally substituted with 1 to 3 fluorine atoms, —$NH_2$, or cyclopropyl;

provided that when $R^2$ and/or $R^3$ are not hydrogen then $R^4$ is hydrogen; and provided that when $R^4$ is not hydrogen then $R^2$ and/or $R^3$ are hydrogen;

provided that $R^5$ may be hydrogen when the sulfur atom is attached to the bicyclo[3.1.0]hexane ring system in the S configuration;

or a pharmaceutically acceptable salt thereof.

2. The compound of claim 1 wherein
$R^1$ is

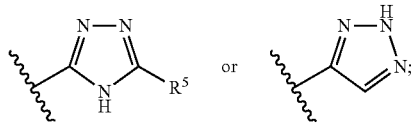

$R^2$ is hydrogen, 2,2-dimethyl-propionyloxymethyl, or benzyl, wherein benzyl is optionally substituted with one to two fluorine atoms, —$C_1$-$C_3$ alkyl optionally substituted with 1 to 3 fluorine atoms, or —$C_1$-$C_3$ alkoxy;

$R^3$ is hydrogen, 2,2-dimethyl-propionyloxymethyl, or benzyl, wherein benzyl is optionally substituted with one to two fluorine atoms, —$C_1$-$C_3$ alkyl optionally substituted with 1 to 3 fluorine atoms, or —$C_1$-$C_3$ alkoxy;

$R^4$ is hydrogen, (2S)-2-aminopropanoyl, (2S)-2-amino-4-methylsulfanyl-butanoyl, (2S)-2-amino-4-methyl-pentanoyl, or 2-aminoacetyl; and $R^5$ is —$C_1$-$C_3$ alkyl optionally substituted with 1 to 3 fluorine atoms, —$NH_2$, or cyclopropyl;

provided that when $R^2$ and/or $R^3$ are not hydrogen then $R^4$ is hydrogen; provided that when $R^4$ is not hydrogen then $R^2$ and $R^3$ are hydrogen;

or a pharmaceutically acceptable salt thereof.

3. The compound according to claim 1
wherein
$R^2$ is 2,2-dimethyl-propionyloxymethyl, or benzyl optionally substituted with one to two fluorine atoms, —$CF_3$, or —$OCH_3$; and $R^3$ is 2,2-dimethyl-propionyloxymethyl, or benzyl optionally substituted with one to two fluorine atoms, —$CF_3$, or —$OCH_3$;

or a pharmaceutically acceptable salt thereof.

4. The compound according to claim 1 wherein $R^1$ is

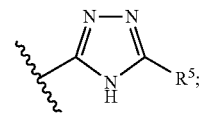

or a pharmaceutically acceptable salt thereof.

5. The compound according to claim 1 wherein $R^2$ and $R^3$ are each is hydrogen, and $R^4$ is other than hydrogen; or a pharmaceutically acceptable salt thereof.

6. The compound according to claim 1 wherein $R^2$, $R^3$ and $R^4$ are each hydrogen; or a pharmaceutically acceptable salt thereof.

7. A pharmaceutical composition comprising a compound according to claim 1, or a pharmaceutically acceptable salt thereof, and a pharmaceutically acceptable carrier, diluent, or excipient.

8. A method of treating a psychiatric disorder selected from the group consisting of bipolar disorder, schizophrenia, and generalized anxiety disorder, comprising administering to a patient in need thereof an effective amount of a compound according to claim 1, or pharmaceutically acceptable salt thereof.

9. The method of claim 8, wherein the psychiatric disorder is bipolar disorder.

10. The method of claim 8, wherein the psychiatric disorder is schizophrenia.

11. The method of claim 8 wherein the psychiatric disorder is generalized anxiety disorder.

* * * * *